United States Patent
Bertozzi et al.

(10) Patent No.: US 11,141,389 B2
(45) Date of Patent: Oct. 12, 2021

(54) AGENTS THAT INHIBIT NGLY1 AND METHODS OF USE THEREOF

(71) Applicant: The Board of Trustees of the Leland Stanford Junior University, Stanford, CA (US)

(72) Inventors: Carolyn Ruth Bertozzi, Stanford, CA (US); Frederick Tomlin, Stanford, CA (US); Ulla Gerling-Driessen, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/482,679

(22) PCT Filed: Jan. 26, 2018

(86) PCT No.: PCT/US2018/015380
§ 371 (c)(1),
(2) Date: Jul. 31, 2019

(87) PCT Pub. No.: WO2018/144327
PCT Pub. Date: Aug. 9, 2018

(65) Prior Publication Data
US 2019/0365677 A1 Dec. 5, 2019

Related U.S. Application Data

(60) Provisional application No. 62/452,808, filed on Jan. 31, 2017.

(51) Int. Cl.
*A61K 31/16* (2006.01)
*A61K 31/165* (2006.01)
*A61P 35/02* (2006.01)
*A61K 31/336* (2006.01)
*A61K 38/07* (2006.01)
*A61K 45/06* (2006.01)

(52) U.S. Cl.
CPC ............ *A61K 31/165* (2013.01); *A61K 31/16* (2013.01); *A61K 31/336* (2013.01); *A61K 38/07* (2013.01); *A61K 45/06* (2013.01); *A61P 35/02* (2018.01)

(58) Field of Classification Search
CPC ...... A61K 31/16; A61K 31/165; C07C 233/01
See application file for complete search history.

(56) References Cited

U.S. PATENT DOCUMENTS

| 6,388,054 B1 * | 5/2002 | Stewart | C07K 5/0205 530/314 |
| 2009/0036390 A1 | 2/2009 | Anderson et al. | |
| 2015/0190456 A1 * | 7/2015 | Li | A61K 31/404 514/19.3 |

FOREIGN PATENT DOCUMENTS

| WO | 2016004221 A1 | 7/2016 | |
| WO | 2016113357 A1 | 7/2016 | |
| WO | WO-2019036417 A2 * | 2/2019 | ........... A61K 31/655 |

OTHER PUBLICATIONS

Davis et al. Synthesis of sansalvamide A peptidomimetics: triazole, oxazole, thiazole, and pseudoproline containing compounds. Tetrahedron. 2012, vol. 68, pp. 1029-1051. (Year: 2012).*
Suzuki et al. Total Synthesis of Bistratamides J, E, and H from Two Type of delta-Ala-Containing Oligopeptides. Bulletin of the Chemical Society of Japan. 2008, vol. 81, No. 4, pp. 495-501. (Year: 2008).*
Tomlin et al. Inhibition of NGLY1 Inactivates the Transcription Factor Nrf1 and Potentiates Proteasome Inhibitor Cytotoxicity. ACS Central Science. Oct. 25, 2017, vol. 3, pp. 1143-1155. (Year: 2017).*
Misaghi et al. (2004) "Using a Small Molecule Inhibitor of Peotide:N-Glyc:anasP.to ProhP. Its RoIF. in 1-4 Glycoprotein Turnover," Chemistry & Biology,vol. 11, Iss. 12, pp. 1677-1687.
Tomlin et al. (2017) "Inhibition of NGL Y1 Inactivates the Transcription Factor Nrf1 and Potentiates 1-4 Proteasome Inhibitor Cytotoxicity," ACS Cent Sci, vol. 3, No. 33, pp. 1143-1155.

* cited by examiner

*Primary Examiner* — Jeffrey E. Russel
(74) *Attorney, Agent, or Firm* — Pamela J. Sherwood; Bozicevic, Field & Francis LLP

(57) ABSTRACT

Methods are provided for treatment of cancer cells, in a regimen comprising contacting the cancer cells with an inhibitor on NGly1, optionally in combination with a direct proteasome inhibitor.

15 Claims, 6 Drawing Sheets
Specification includes a Sequence Listing.

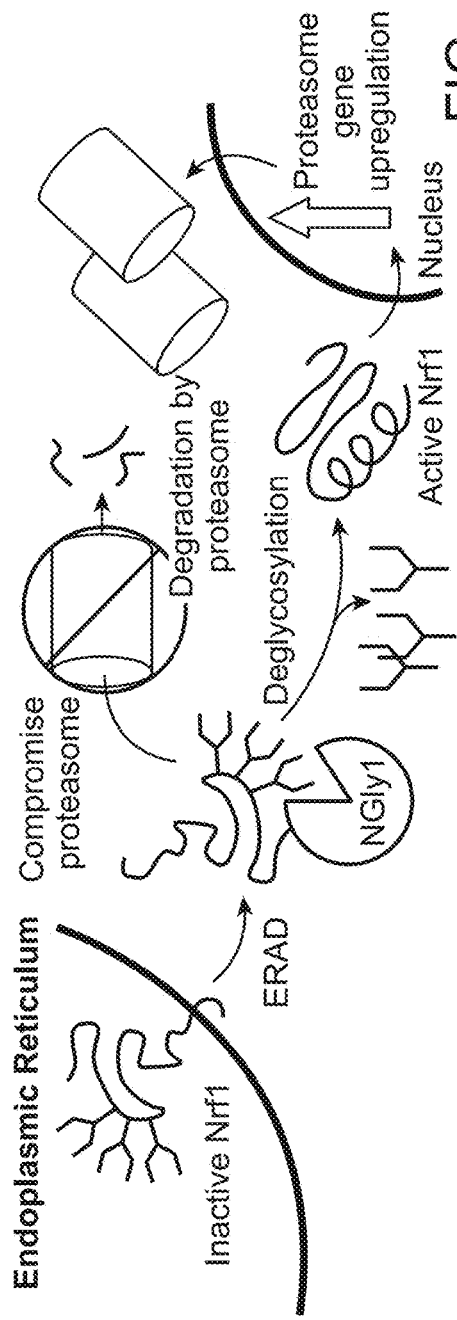
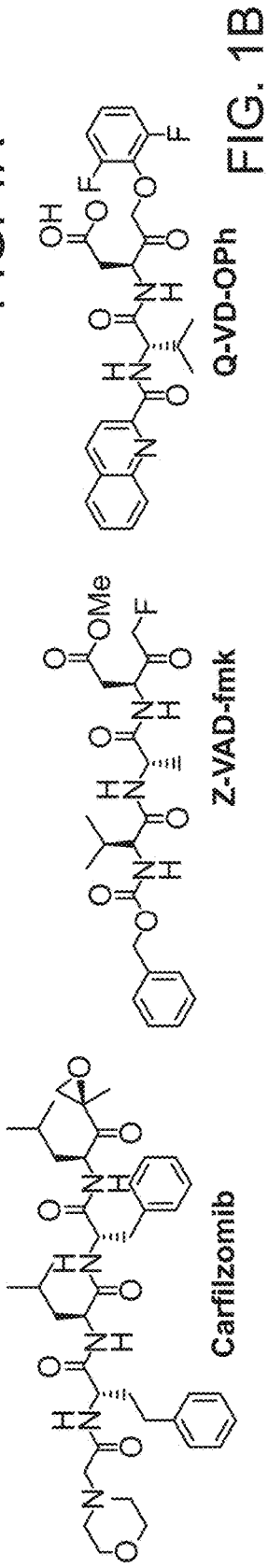
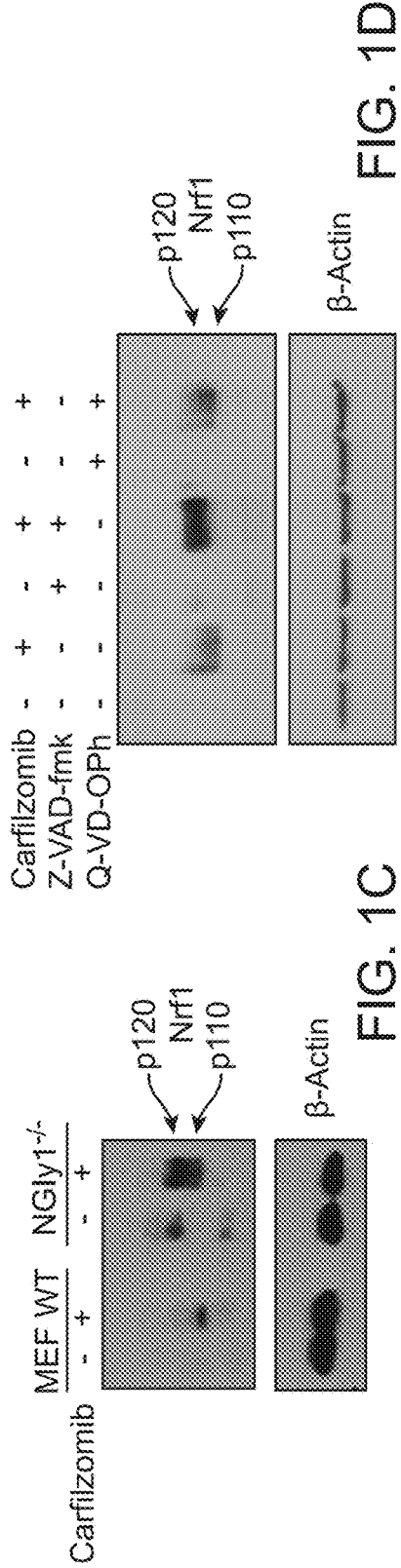
FIG. 1A
FIG. 1B
FIG. 1C
FIG. 1D

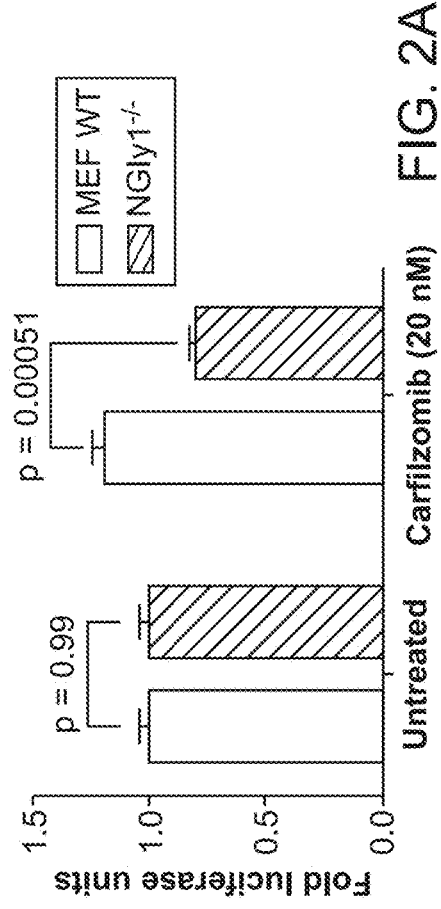
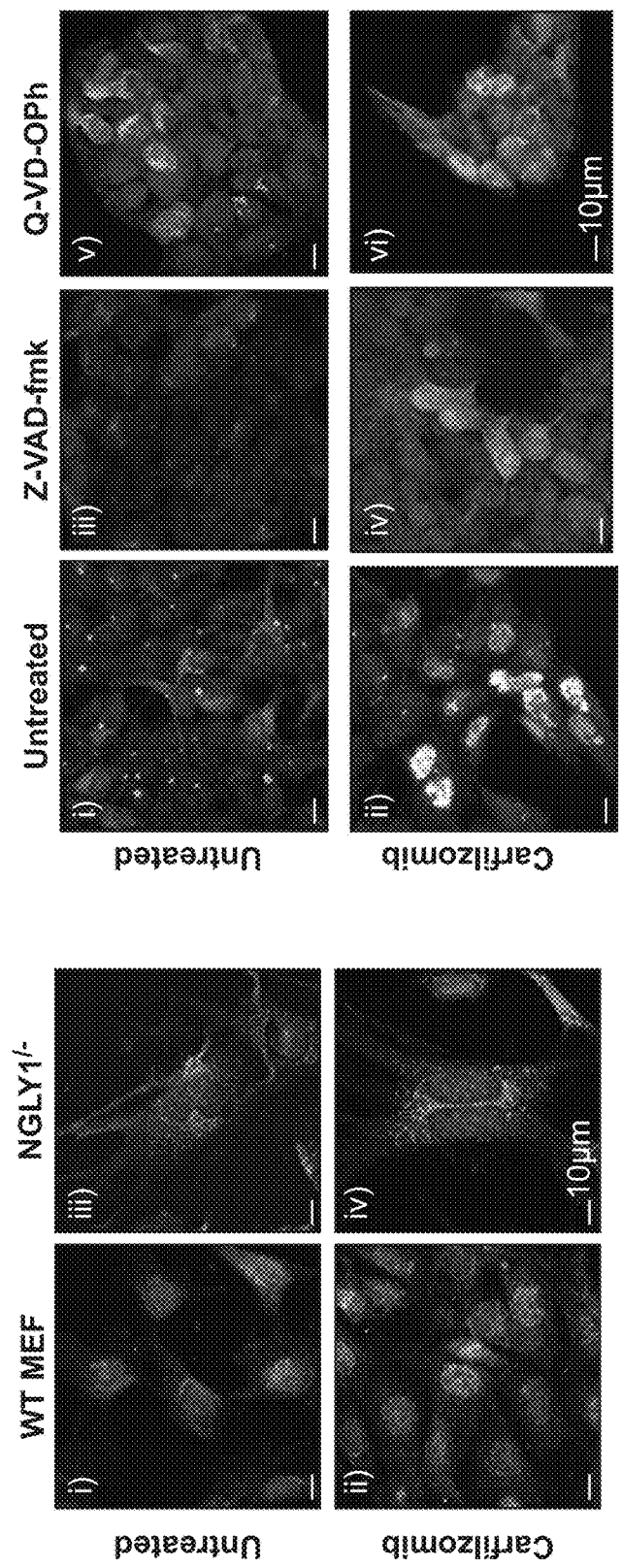
FIG. 2A
FIG. 2B
FIG. 2C

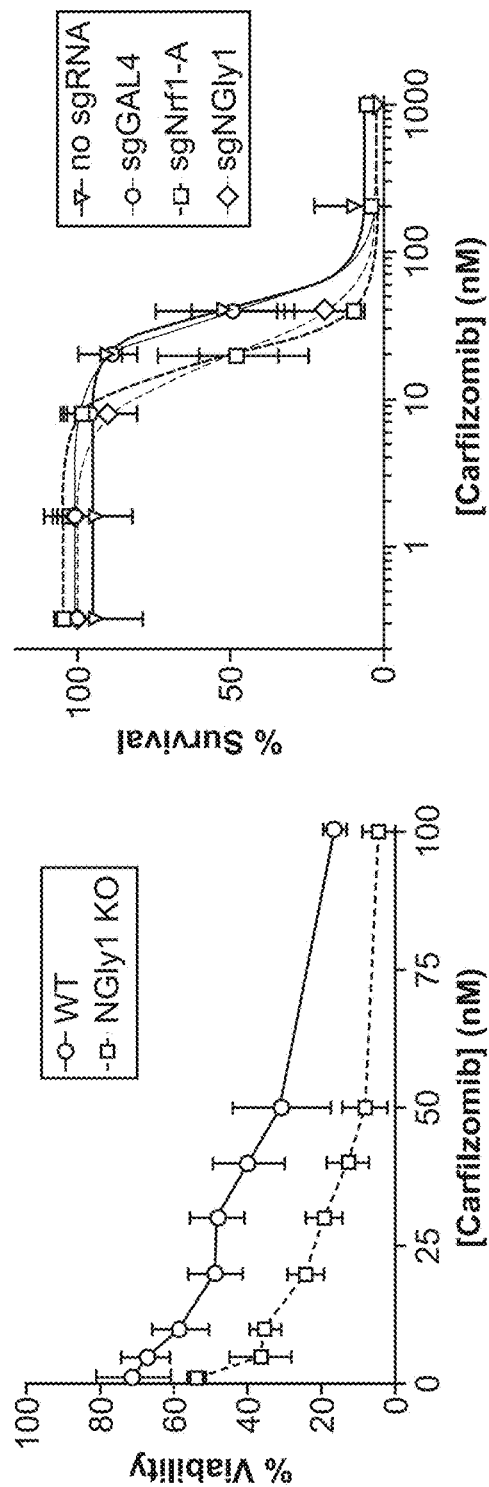
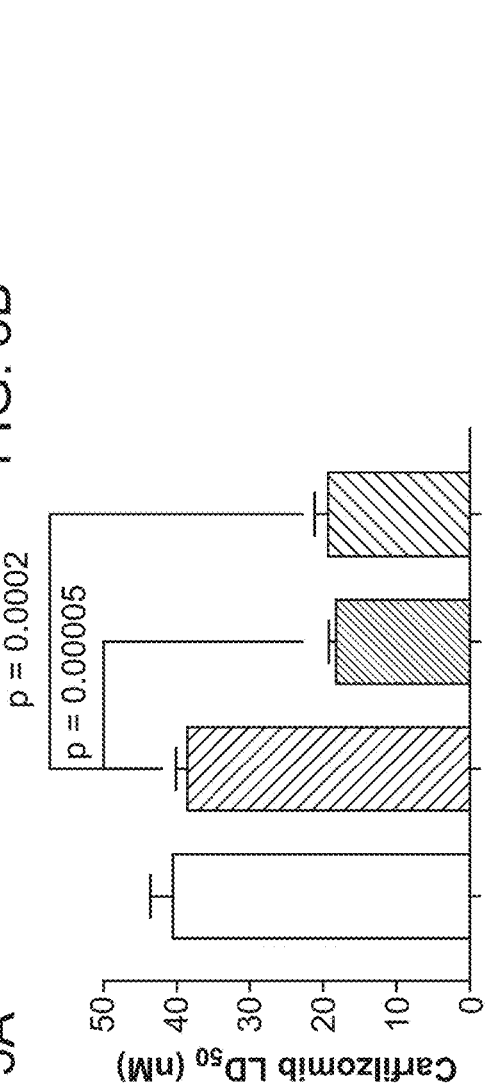
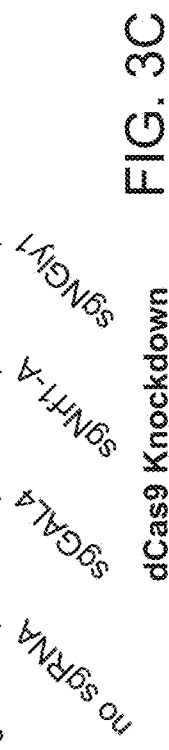
FIG. 3A
FIG. 3B
FIG. 3C

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: synthetic nucleic acid

<400> SEQUENCE: 1
gaagctccgg cgccgagagt                                                    20

<210> SEQ ID NO 2
<211> LENGTH: 20
<212> TYPE: DNA
<213> ORGANISM: Artificial sequence
<220> FEATURE:
<223> OTHER INFORMATION: synthetic nucleic acid

<400> SEQUENCE: 2
gtgaggcgcc tgctcagtgt                                                    20

<210> SEQ ID NO 3
<211> LENGTH: 21
<212> TYPE: DNA
<213> ORGANISM: Artificial sequence
<220> FEATURE:
<223> OTHER INFORMATION: synthetic nucleic acid

<400> SEQUENCE: 3
gaacgactag ttaggcgtgt a                                                  21

<210> SEQ ID NO 4
<211> LENGTH: 23
<212> TYPE: DNA
<213> ORGANISM: Artificial sequence
<220> FEATURE:
<223> OTHER INFORMATION: synthetic nucleic acid

<400> SEQUENCE: 4
ggtggtctcc tctgacttca aca                                                23

<210> SEQ ID NO 5
<211> LENGTH: 23
<212> TYPE: DNA
<213> ORGANISM: Artificial sequence
<220> FEATURE:
<223> OTHER INFORMATION: synthetic nucleic acid

<400> SEQUENCE: 5
gttgctgtag ccaaattcgt tgt                                                23

<210> SEQ ID NO 6
<211> LENGTH: 20
```

```
<212> TYPE: DNA
<213> ORGANISM: Artificial sequence
<220> FEATURE:
<223> OTHER INFORMATION: synthetic nucleic acid

<400> SEQUENCE: 6
agtggcaaga tctcatgtcc                                                  20

<210> SEQ ID NO 7
<211> LENGTH: 22
<212> TYPE: DNA
<213> ORGANISM: Artificial sequence
<220> FEATURE:
<223> OTHER INFORMATION: synthetic nucleic acid

<400> SEQUENCE: 7
gctgaagagt aagaagtcct gg                                               22

<210> SEQ ID NO 8
<211> LENGTH: 21
<212> TYPE: DNA
<213> ORGANISM: Artificial sequence
<220> FEATURE:
<223> OTHER INFORMATION: synthetic nucleic acid

<400> SEQUENCE: 8
aatatctggg tcagtggctt g                                                21

<210> SEQ ID NO 9
<211> LENGTH: 21
<212> TYPE: DNA
<213> ORGANISM: Artificial sequence
<220> FEATURE:
<223> OTHER INFORMATION: synthetic nucleic acid

<400> SEQUENCE: 9
cattttccac acgccattct c                                                21

<210> SEQ ID NO 10
<211> LENGTH: 110
<212> TYPE: DNA
<213> ORGANISM: Artificial sequence
<220> FEATURE:
<223> OTHER INFORMATION: synthetic nucleic acid

<400> SEQUENCE: 10
cgagccgtgg gcacgatgac tctgcaccgc ctcctctgag ccgtgggcac gatgactctg      60
caccgcctcc tctgagccgt gggcacgatg actctgcacc gcctcctctg                110
```

AGENTS THAT INHIBIT NGLY1 AND METHODS OF USE THEREOF

CROSS-REFERENCE TO RELATED APPLICATIONS

This application claims priority to U.S. Ser. No. 62/452,808, filed Jan. 31, 2017, the contents of each of which is incorporated herein by reference.

BACKGROUND

The ubiquitin-proteasome pathway holds an essential role in maintaining normal cellular homeostasis since it is responsible for the degradation of proteins in eukaryotic cells, including regulatory proteins that control cell-cycle progression, apoptosis, and DNA repair. Disrupting the proteasome activity results in the rapid accumulation of incompatible regulatory proteins within the cell, which induce an apoptotic cascade that leads to growth arrest and finally cell death. Since cancer cells in general have higher levels of proteasome activity compared to normal cells and show a higher sensitivity to the proapoptotic effects of proteasome inhibition, the proteasome has become a potent target in oncology.

The balance of protein synthesis and degradation is tightly regulated in healthy, normal cells. Most intracellular proteins are degraded via the ubiquitin-proteasome system (UPS), in which proteins are tagged by ubiquitin and then recognized by the 26S proteasome complex, which degrades them into small peptides. The UPS is responsible for degrading 80-90% of intracellular proteins. Proteins targeted for proteasomal degradation are ubiquitinated by a series of enzymes, including the ubiquitin-activating enzyme E1, ubiquitin-conjugating enzyme E2, and the ubiquitin E3 ligases, which allow the targeted proteins to be recognized by the 26S proteasome (MW 2,400 kDa), a multi-subunit protease complex composed of the 20S catalytic core (MW 700 kDa) and one or two 19S regulatory particles (MW 700 kDa). The 20S core is formed by two sets of identical $\alpha$ rings and two sets of identical $\beta$ rings stacked in a symmetrical manner with the outside $\alpha$ rings surrounding the inner $\beta$ rings ($\alpha\beta\beta\alpha$). Each $\alpha$ or $\beta$ ring contains seven different subunits, named $\alpha 1$-$\alpha 7$ or $\beta 1$-$\beta 7$, respectively, among which mainly $\beta 1$, $\beta 2$, and $\beta 5$ possess proteolytic activity. The $\beta 1$ subunit is responsible for caspase-like (or peptidyl-glutamyl peptide-hydrolyzing-like/PGPH-like) activity that preferentially cleaves after acidic residues (e.g., aspartate and glutamate), the $\beta 2$ subunit has trypsin-like activity that preferentially cleaves after basic residues (e.g., arginine and lysine), and the $\beta 5$ subunit has chymotrypsin-like activity preferentially cleaving after hydrophobic residues (e.g., tyrosine and phenylalanine). The 19S regulatory particle is composed of a "lid" and a "base", and binds to both ends of the 20S core proteasome. The 19S proteasome lid contains nine or more non-ATPase subunits, which recognize polyubiquitinated proteins, bind them, and remove the polyubiquitin chain from the substrate proteins by a process called deubiquitination. Meanwhile, the 19S base contains six ATPase and four non-ATPase subunits responsible for the unfolding of substrate proteins and promotion of their entry into the 20S proteasome.

Dysregulation of protein degradation plays an essential role in the cell growth, development and survival of human cancer. Proteasomal mRNA levels are consistently markedly increased in a variety of malignant human hematopoietic cell lines compared with peripheral lymphocytes and monocytes from healthy adults. Also, increased proteasome activity is associated with malignant disease, including those of the colon, prostate, and leukemia. Tumorigenic cells are more dependent upon proteasomal activity and thus more sensitive to its blockage. Indeed, researchers found that many types of actively proliferating tumor cells are more sensitive to proteasome inhibitors than non-tumorigenic cells. Pharmacological inhibition of the proteasome results in the shift in balance of pro- and anti-apoptotic proteins, including the accumulation of tumor suppressor proteins, resulting in cell cycle arrest and apoptosis. In some tumor cell types, proteasome inhibitors exhibit more effective apoptosis-inducing capability compared to standard cytotoxic agents. Proteasome inhibition is found to be an effective strategy for chemosensitization and overcoming resistance.

In particular, the treatment of hematologic malignancies such as multiple myeloma have improved significantly by the use of proteasome inhibitors. Bortezomib, a dipeptidyl boronic acid derivative that reversibly targets the chymotrypsin-like active site of the $\beta 5$-subunit of the 20S proteasome, was the first FDA approved proteasome inhibitor for the treatment of cancer, for example multiple myeloma (MM) and mantle cell lymphoma (MCL). Proteasome inhibition with bortezomib results in growth suppression and apoptosis of the tumor cells, inhibits the activation of NF-$\kappa$B in cells and tumor microenvironment, blocks production and intracellular signaling of IL-6, stops the production of and expression of proangiogenic mediators and overcomes defects in apoptotic regulators such as Bcl-2, and triggers p53-induced apoptosis.

Bortezomib was able to improve relapse times for MM, albeit with side effects such as peripheral neuropathy and gastrointestinal distress. In addition, increasing intrinsic and acquired resistance to bortezomib spurred the development of second-generation proteasome inhibitors such as the epoxyketone carfilzomib. In comparison to bortezomib, carfilzomib irreversibly inhibits the chymotrypsin-like active site with higher selectivity and shows lower affinity to trypsin- and caspase-like proteases and has minimal activity against off-target enzymes, such as serine proteases. In addition, it has shown activity against bortezomib-resistant cell lines and primary MM cells.

Although proteasome inhibitors have improved the treatment of MM, developed resistances and short periods of response require new therapeutic avenues.

SUMMARY

Compositions and methods are provided for the treatment of cancer through inhibition of transcription factor pathways involved in proteasome expression. In particular, compositions and methods of use thereof are provided for inhibition of N-Glycanase1 (NGly1). Inhibition of NGly1 reduces proteasome expression. The NGly1 inhibitor may be used as a single agent, or in combination with an agent that directly inhibits proteasome activity. The combination of agents may provide for increased overall survival of an individual being treated for cancer. The combination of agents may provide for a synergistic benefit in killing of cancer cells, relative to administration as a single agent.

In some embodiments, compounds and formulations thereof are provided of NGly1 inhibitors. In some embodiments the compound inhibits NGly1 and does not inhibit caspase activity. In some embodiments the inhibitor inhibits Ngly1 mechanistically by inhibiting nucleophilic attack of a cysteine residue at the amide linkage between the asparagine side chain of the target protein and the N-linked oligosaccharide. In some embodiments a pharmaceutical formulation is provided of an NGly1 inhibitor with a pharmaceutically acceptable excipient. In some embodiments the formulation is provided in a unit dose formulation, providing a dose effective to reduce proteasome expression in a targeted cell. In some embodiments the formulation further comprises an effective dose of a drug that directly inhibits proteasome activity.

In some embodiments the NGly1 inhibitor has a structure of formula I.

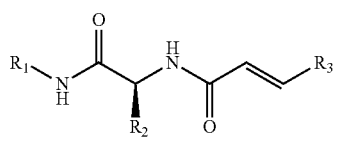

where $R_1$ is H, alkyl including lower alkyls, branched alkyls, substituted alkyls, aryl, alkaryl, substituted aryl, substituted alkaryl, etc.;

$R_2$ is H, alkyl including lower alkyls, branched alkyls, substituted alkyls, aryl, alkaryl, substituted aryl, substituted alkaryl, etc.; and $R_3$ is alkyl including lower alkyls, branched alkyls, substituted alkyls, aryl, alkaryl, substituted aryl, substituted alkaryl, an electron withdrawing substituent, or an electron donating group. In some embodiments a candidate NGly1 inhibitor is tested for activity based on inhibiting deglycosylation of a polypeptide substrate comprising a site for N-glycosylation. In some such embodiments the assay is a fluorescent assay.

In other embodiments, methods are provided for treating cancer, which cancers include without limitation hematologic cancers, e.g. leukemias, lymphomas, myelomas, etc.; solid tumors including without limitation, carcinomas such as adenocarcinomas, squamous cell carcinomas, basal cell carcinomas, renal cell carcinomas; gliomas; sarcomas; melanomas. In some embodiments the cancer is multiple myeloma. In the methods of the invention, cancer cells are contacted with an effective dose of an NGly1 inhibitor, which dose is effective to reduce expression of the proteasome in the targeted cells. In some embodiments the cancer cells are also contacted with an effective dose of a direct proteasome inhibitor, which inhibitor may include, without limitation, one or more of bortezomib, carfilzomib, ixazomib, delanzomib, oprozomib, marizomib, IPSI-001, ONX-0914, PR-924, etc.

In some embodiments an effective dose of a combination of agents is administered to treat cancer, of (i) an NGly1 inhibitor; and (ii) a direct proteasome inhibitor. The agents in the combination may be administered concomitantly, i.e. each agent is administered within about 45 days, 30 days, 15 days, 7 days, 3 days, 2 days, 1 day or substantially simultaneously with respect to the other agent(s) in the combination. A benefit of the present invention may be the use of lowered doses of the proteasome inhibitor relative to the dose required as a monotherapy, for example to provide for reduced side effects, e.g. peripheral neuropathy. Administration may be repeated as necessary for depletion of the cancer cell population. A benefit may be reduced resistance to the proteasome inhibitor, such that administration is effective over a longer period of time.

The contacting of a cancer cells may be performed in vivo, e.g. for therapeutic purposes, and in vitro, e.g. for screening assays and the like. The combination therapy can be synergistic in enhancing elimination of tumor cells as compared to the use of single agents. Further, the combination can provide for increased overall survival of the individual that is treated.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1D. NGly1 is required for the correct processing of Nrf1. FIG. 1A Proposed pathway of De-N-glycosylation-dependent Nrf1 activation for proteasomal bounce-back. FIG. 1B Chemical structures of carfilzomib, a proteasome inhibitor; Z-VAD-fmk, an NGly1 inhibitor that also functions as a pan-caspase inhibitor; Q-VD-OPh, a pan-caspase inhibitor that does not inhibit NGly1. FIG. 1C NGly1$^{-/-}$ MEF cells display abnormal processing of Nrf1 in the presence of the proteasome inhibitor carfilzomib. FIG. 1D Inhibition of NGly1 by Z-VAD-fmk causes Nrf1 to be incorrectly processed in Nrf1 overexpressing HEK cells. The caspase inhibitor Q-VD-OPh shows similar processing to untreated cells.

FIG. 2A-2C. NGly1 is required for the activation and correct subcellular localization of Nrf1. FIG. 2A In a Nrf1-dependent luciferase reporter assay, NGly1$^{-/-}$ MEFs displayed a lesser response to proteasome inhibition compared to WT MEFs. FIG. 2B Localization of Nrf1 is altered in NGly1$^{-/-}$ compared to WT: i) untreated WT; ii) WT in presence of 20 nM carfilzomib; iii) untreated NGly1$^{-/-}$; iv) NGly1$^{-/-}$ in presence of 20 nM carfilzomib. FIG. 2C Localization of Nrf1 is altered in Nrf1 overexpressing HEK cells treated with Z-VAD-fmk: i) Untreated; ii) treated with 10 nM carfilzomib; iii) treated with 100 μM Z-VAD-fmk; iv) treated with 100 μM Z-VAD-fmk and 10 nM carfilzomib; v) treated with 50 nM Q-VD-Oph; vi) treated with 50 nM Q-VD-OPh and 10 nM carfilzomib.

FIG. 3A-3C. NGly1$^{-/-}$ or NGly1 knockdown increases sensitivity of cells to proteasome inhibitors. FIG. 3A Viability of MEF NGly1$^{-/-}$ is significantly lower than MEF WT after 24 hours incubation with proteasome inhibitor carfilzomib. FIG. 3B Knockdown of NGly1 or Nrf1 by dCas9-sgRNA in K562 reduces survival during treatment with proteasome inhibitor. FIG. 3C The LD$_{50}$ of carfilzomib in K562 cells is decreased ~2 fold with Nrf1 or NGly1 knockdown.

FIG. 4A Schematic of the Cresswell assay for detection of NGly1 inhibition. FIG. 4B Six hits obtained from the high-throughput screen. FIG. 4C Validation of the hits in the Cresswell assay. Only WRR139 was found to inhibit NGly1 in a dose-dependent manner. FIG. 4D In the presence of WRR139, RNAseB is not deglycosylated by recombinant NGly1.

FIG. 5A Survival is significantly reduced in U266 cells in the presence of WRR139. FIG. 5B Survival is significantly reduced in H929 cells in the presence of WRR139. FIG. 5C The LD$_{50}$ of carfilzomib treatment is reduced by 2.6 and 2 fold, respectively in U266 and H929.

DETAILED DESCRIPTION OF THE EMBODIMENTS

Figure 4A:
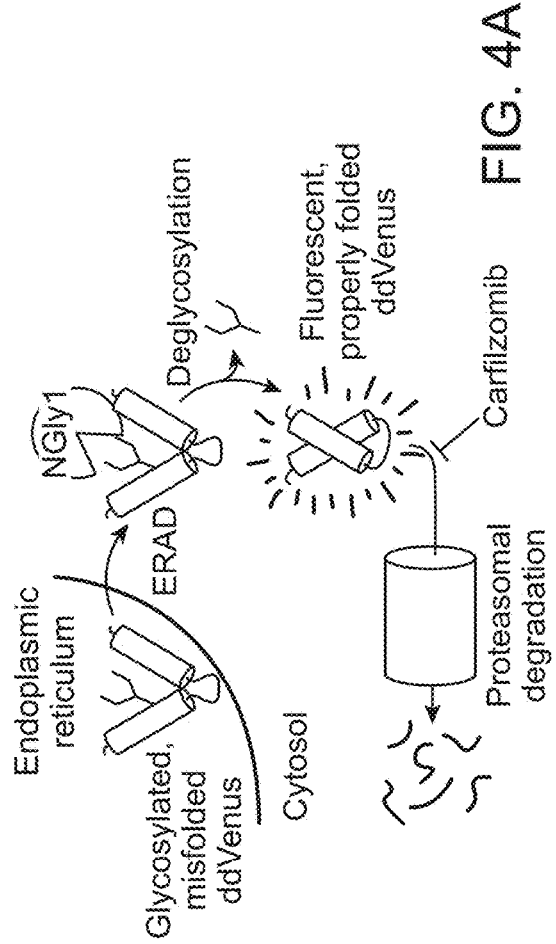
FIG. 4A-4D. A targeted screen of cysteine protease inhibitor-like compounds led to the discovery of novel NGly1 inhibitor WRR139.

Methods are provided for the depletion of cancer cells in a subject, where the cancer cells are contacted with an effective dose of an NGly1 inhibitor, optionally in combination with a direct proteasome inhibitor. Additional chemotherapeutic drugs may also be provided. Cancers include without limitation hematologic cancers, e.g. multiple myeloma, mast cell lymphoma, Waldenstrom's Macroglobulinemia (WM); non-Hodgkin's lymphomas such diffuse large B-cell lymphoma (DLBCL) cutaneous T cell lymphoma, etc.; acute leukemias such as acute myeloid leukemia (AML), acute lymphocytic leukemia; chronic leukemias such as chronic myeloid leukemia and chronic lymphocytic leukemia; etc.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

NGly1 inhibitor. Certain inhibitors of NGly1 are disclosed herein; and other inhibitors, including without limitation Z-VAD-FMK (carbobenzoxy-valyl-alanyl-aspartyl-[O-methyl]-fluoromethylketone) are known in the art, or may be determined through a screening assay as described herein in the Examples. In some embodiments the compound inhibits NGly1 and does not inhibit caspase activity. In some embodiments the inhibitor inhibits Ngly1 mechanistically by inhibiting nucleophilic attack of a cysteine residue at the amide linkage between the asparagine side chain of the target protein and the N-linked oligosaccharide. In some embodiments a candidate NGly1 inhibitor is tested for activity based on inhibiting deglycosylation of a polypeptide substrate comprising a site for N-glycosylation. In some such embodiments the assay is a fluorescent assay.

In some embodiments an NGly1 inhibitor has a structure of formula I.

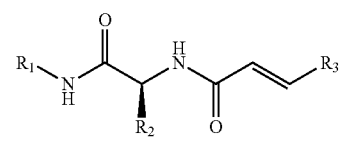

I where $R_1$ is H, $R_2$ is H, alkyl including lower alkyls, branched alkyls, substituted alkyls, aryl, alkaryl, substituted aryl, substituted alkaryl, etc.; and $R_3$ is alkyl including lower alkyls, branched alkyls, substituted alkyls, aryl, alkaryl, substituted aryl, substituted alkaryl, an electron withdrawing substituent, or an electron donating group.

In some such embodiments, $R_3$ is a halogen, depicted as X in structure II below

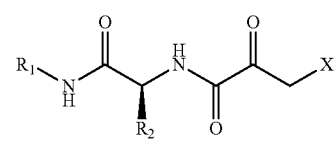

II where X is a chloro, bromo, fluoro or iodo substituent.

In some embodiments an NGly1 inhibitor has a structure of Formula III, where $R_1$ and $R_2$ are as described above, and

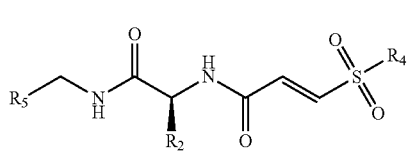

III $R_4$ is an alkyl group, including lower alkyls, e.g. methyl, ethyl, propyl, isopropyl, etc.

$R_5$ is polar or non-polar group, including but not limited to alkynyl, alkenyl, morpholino, amino, amido, sulfhydryl, etc.

In some embodiments an NGly1 inhibitor has a structure of Formula IV where $R_4$ and $R_5$ are as described above, and

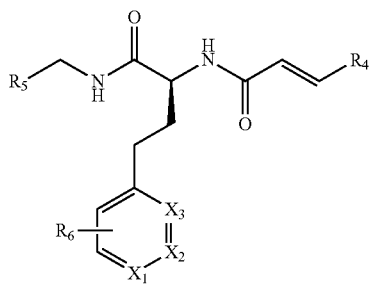

IV $R_6$ is an optional substituent on the aryl ring in any location (ortho, meta, or para), which substitutent may be alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, or fused heterocycle;

Any of $X_1$, $X_2$ and $X_3$ are optionally a heteroatom selected from nitrogen, oxygen, sulfur, phosphorus or silicon, typically nitrogen, oxygen or sulfur.

In some embodiments the NGly1 inhibitor is an epoxyketone of Formula V

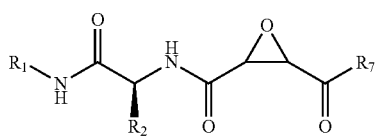

V where $R_7$ is an amine, substituted amine, amide, substituted amide, alkyl including lower alkyls, branched alkyls, substituted alkyls, aryl, alkaryl, substituted aryl, substituted alkaryl, etc.

Drug screening may be performed using an in vitro model, a genetically altered cell or animal, or purified NGly1 protein to identify inhibitors. A wide variety of assays may be used for this purpose, including labeled in vitro protein-protein binding assays, electrophoretic mobility shift assays, immunoassays for protein binding, and the like. The term "agent" as used herein describes any molecule, e.g. protein or pharmaceutical, with the capability of inhibiting the physiological function of NGly1. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay or an activity assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

As an example of a suitable assay, a protein with a detectable phenotype, including without limitation a fluorescent protein, is mutated to misfold and contain a site for N-glycosylation. The protein is then only properly folded upon deglycosylation by NGly1. Thus inhibition of NGly1 results in a lack of the detectable phenotype. In one embodiment, the misfolded protein is a fluorescent protein, such as ddVenus.

Proteasome inhibitors. Direct proteasome inhibitors bind to a component of the proteasome and reversibly or irreversibly block enzymatic activity. Such inhibitors are known in the art and clinically used or are in the process of being tested in clinical trials. It will be understood by one of skill in the art that the class of agents is known in used, and that specific members described below are exemplary but not limiting.

Direct proteasome inhibitors include bortezomib (BTZ; β-methyl-1-[3-phenyl-2-pyrazin-2-ylcarbonylamino-propanoyl) amino-butyl] boronic acid), which is a dipeptide boronic acid derivative containing pyrazinoic acid, phenylalanine and leucine with boronic acid in its structure. BTZ is a reversible inhibitor of the 20S proteasome. The boronic acid group of BTZ binds and forms a complex with the active site of threonine hydroxyl group in the β5-subunit, blocking the chymotrypsin-like activity of the proteasome. It also binds the β1 subunit with lower affinity, inhibiting its PGPH-like activity. Pharmacodynamic studies showed dose-dependent inhibition of proteasome activity by BTZ with intravenous doses ranging from 0.13 to 2.0 mg/m$^2$, with peak inhibition occurring within one hour after dosing. Currently approved indications include multiple myeloma and mast cell lymphoma, and it has shown activity against Waldenstrom's Macroglobulinemia (WM); diffuse large B-cell lymphoma (DLBCL);and acute myeloid leukemia (AML).

BTZ may be combined with several other classes of drugs used in the treatment of hematologic malignancies, including alkyating agents, anthracyclines, and immunomodulatory drugs; for example BTZ+DEX; BTZ+melphalan+DEX; BTZ+DEX+pegylated doxorubicin; PAD; VDD; VTD; VMP; CyBorD, RVD; VTD-PACE; etc.

Carfilzomib (CFZ, also called PR-171, marketed as Kyprolis®) is an irreversible peptide epoxyketone class proteasome inhibitor. The α,β-epoxyketone moiety interacts with both the hydroxyl group and the free α-amino group of Thr1 in the catalytic β subunits of the proteasome, leading to the formation of the morpholino adduct in an irreversible fashion. The irreversible binding by epoxyketone-based proteasome inhibitors leads to more sustained as activity compared to BTZ, as new subunit synthesis and proteasome assembly are required for restoration of proteasome activity. Proteasome activity in blood and PBMCs was inhibited by CFZ in a dose-dependent manner, >75% inhibition at 15 mg/m$^2$ after the first dose, and >90% inhibition after five doses. Combinations include, for example, CFZ, lenalidomide, and DEX.

Ixazomib (MLN-9708) is an orally bioavailable boronic ester prodrug and reversible proteasome inhibitor. It is currently being tested in many clinical trials in a wide range of clinical indications, including previously untreated MM, relapsed MM, advanced stage solid tumors, lymphoblastic leukemia, non-Hodgkin's lymphoma, and AL amyloidosis. Delanzomib (DLZ) is another reversibly binding boronate-based, second-generation proteasome inhibitor with both oral and IV bioavailability. DLZ has shown proteasome-inhibitory activity similar to that of BTZ in hematologic and solid tumor cell lines, as well as in primary cells front multiple myeloma patients. Oprozomib (OPZ) is an orally bioavailable peptide epoxyketone-based, irreversible proteasome inhibitor that showed similar potency to CFZ in cytotoxicity assays. Marizomib is an irreversible proteasome inhibitor with a β-lactone backbone. The carbonyl group of the β-lactone can interact with the hydroxyl group of Thr1 in catalytic β subunits, leading to the formation of an acyl-ester adduct. This process is reversible, but the covalent adduct only dissociates at a very slow rate. In addition to the acyl-ester bond, marizomib also forms a cyclic tetrahydrofuran ring with the proteasome, making the reaction irreversible.

Immunoproteasome Specific Inhibitor-001 (IPSI-001) preferably inhibits the immunoproteasome 20S$_i$ activity (mainly by binding to β 1$_i$ subunit) over the constitutive 20S proteasome activity, potently suppressing proliferation and inducing apoptosis in MM cell lines as well as in patient samples. ONX-0914 and PR-924 are peptide epoxyketone-based immunoproteasome inhibitors, both of which are able to selectively and irreversibly inhibit the β5i subunit ONX-0914 is 20 to 40-fold more selective towards the β5i subunit than both the β5 and β1i subunits.

In some embodiments, when combined with an Ngly1 inhibitor, the dose of a direct proteasome inhibitor is reduced to a level that minimizes undesirable side effects, e.g. at a dose that is up to about 90% of the currently approved dose, up to about 80%, up to about 70%, up to about 60%, up to about 50%, up to about 40%, up to about 30%, up to about 20%, up to about 10%, up to about 5% of a conventional dose. In some embodiments, when combined with an Ngly1 inhibitor, the number of doses is reduced. For some patients, proteasome inhibitors cause toxic peripheral neuropathy, which is one of the limiting side effects of these treatments, and which thus curtails its potential effectiveness. For example, the incidence of neuropathy induced by bortezomib is around 30-60%. Although the neurotoxic mechanisms are not completely understood, studies suggest that aggresome formation, endoplasmic reticulum stress, mitotoxicity, inflammatory response, and DNA damage contribute to this neurotoxicity. In some embodiments of the invention a method is provided for treating cancer with a combination of an agent that inhibits NGly1 and a direct proteasome inhibitor, where the dosing of agents in the combination provides for a treatment of cancer with a clinically significant reduction in neurologic adverse events relative to the dosing required for a direct proteasome inhibitor in the absence of an NGly1 inhibitor.

In some embodiments, an individual is selected for treatment with a combination of an NGly1 inhibitor and a direct proteasome inhibitor where the individual was previously treated with a direct proteasome inhibitor and has become resistant to the direct proteasome inhibitor.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell.

Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

Hematologic cancers are of particular interest, i.e. cancers of cells of hematologic origin such as leukemias, lymphomas and myelomas. Acute leukemias are rapidly progressing leukemia characterized by replacement of normal bone marrow by blast cells of a clone arising from malignant transformation of a hematopoietic cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas).

Polycythemia vera (PV) is an idiopathic chronic myeloproliferative disorder characterized by an increase in Hb concentration and RBC mass (erythrocytosis). PV occurs in about 2.3/100,000 people per year; more often in males (about 1.4:1). Myelodysplastic syndrome (MDS) is a group of syndromes (preleukemia, refractory anemias, Ph-negative chronic myelocytic leukemia, chronic myelomonocytic leukemia, myeloid metaplasia) commonly seen in older patients. Exposure to carcinogens may by be implicated. MDS is characterized by clonal proliferation of hematopoietic cells, including erythroid, myeloid, and megakaryocytic forms. The MDS clone is unstable and tends to progress to AML.

Non-Hodgkin lymphomas are a heterogeneous group of disorders involving malignant monoclonal proliferation of lymphoid cells in lymphoreticular sites, including lymph nodes, bone marrow, the spleen, the liver, and the GI tract. Compared with Hodgkin lymphoma, there is a greater likelihood of disseminated disease at the time of diagnosis. Most (80 to 85%) NHLs arise from B cells; the remainder arise from T cells or natural killer cells. Either precursor or mature cells may be involved. Overlap exists between leukemia and NHL because both involve proliferation of lymphocytes or their precursors. Among the lymphomas within this group are: precursor B-lymphoblastic leukemia/lymphoma; B-cell chronic lymphocytic leukemia/small lymphocytic lymphoma; B-cell prolymphocytic leukemia; Lymphoplasmacytic lymphoma; Splenic marginal zone B-cell lymphoma (±villous lymphocytes); Hairy cell leukemia; Plasma cell myeloma/plasmacytoma; Extranodal marginal zone B-cell lymphoma of the MALT type; Nodal marginal zone B-cell lymphoma (±monocytoid B cells); Follicular lymphoma; Mantle cell lymphoma; Diffuse large B-cell lymphomas; Burkitt's lymphoma; Precursor T-lymphoblastic lymphoma/leukemia; T-cell prolymphocytic leukemia; T-cell granular lymphocytic leukemia; Aggressive NK cell leukemia; Adult T-cell lymphoma/leukemia (HTLV 1-positive); Extranodal NK/T-cell lymphoma, nasal type; Enteropathy-type T-cell lymphoma; Hepatosplenic γ-δ T-cell lymphoma; Subcutaneous panniculitis-like T-cell lymphoma; Mycosis fungoides/Sézary syndrome; Anaplastic large cell lymphoma, T/null cell, primary cutaneous type; Anaplastic large cell lymphoma, T-/null-cell, primary systemic type; Peripheral T-cell lymphoma, not otherwise characterized; Angioimmunoblastic T-cell lymphoma.

Chronic leukemia usually manifests as abnormal leukocytosis with or without cytopenia in an otherwise asymptomatic person. Findings and management differ significantly between chronic lymphocytic leukemia (CLL) and chronic myelocytic leukemia (CML). The most common type of leukemia in the Western world, CLL involves mature-appearing defective neoplastic lymphocytes (almost always B cells) with an abnormally long life span. The peripheral blood, bone marrow, spleen, and lymph nodes undergo leukemic infiltration.

Multiple myeloma is a cancer of plasma cells that produce monoclonal immunoglobulin and invade and destroy adjacent bone tissue. Common manifestations include bone pain, renal insufficiency, hypercalcemia, anemia, and recurrent infections. Diagnosis requires demonstration of M-protein (sometimes present in urine and not serum) and either lytic bone lesions, light-chain proteinuria, or excessive marrow plasma cells. A bone marrow biopsy is usually needed. Currently treatment may include conventional chemotherapy with the addition of bortezomib, lenalidomide, thalidomide, corticosteroids, and high-dose melphalan followed by autologous peripheral blood stem cell transplantation.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. A dose effective to treat cancer includes the depletion or reduction of viable cancer cells due to the activity of the agent in inducing apoptosis or other forms of cell death.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Concomitant administration" of one or more cancer therapeutic drug(s) with a pharmaceutical composition of the present invention means administration with the agent at such time that both agents will have a therapeutic effect. Such concomitant administration may involve concurrent (i.e. at the same time), prior, or subsequent administration of the drug with respect to the administration of a compound of the invention. A person of ordinary skill in the art would have no difficulty determining the appropriate timing, sequence and dosages of administration for particular drugs and compositions of the present invention.

As used herein, endpoints for cancer treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" or "unit dose" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

In addition to proteasome inhibitors, a cancer patient may also be treated with additional treatment modalities, including surgery, radiation therapy, and chemotherapy. Chemotherapeutic agents include without limitation, alkyating agents, anthracyclines, immunomodulatory drugs, corticosteroids, vinca alkyloids, taxanes, epipodophyllotoxins, anthracyclines, actinomycin, etc. Anthracyclines include daunorubicin hydrochloride (daunomycin, rubidomycin, cerubidine), doxorubicin, epirubicin, idarubicin, and mitoxantrone. Vinca alkyloids are a class of drugs originally derived from the Vinca plant, and include vinblastine, vincristine, vindesine, vinorelbine. Taxanes are diterpenes, including paclitaxel and docetaxel. Epipodophyllotoxins are naturally occurring alkaloids, and derivatives thereof. Epipodophyllotoxin derivatives currently used in the treatment of cancer include etoposide, teniposide. Quinoline alkaloids include camptothecin, SN-38, DX-8951f, topotecan, 9-aminocamptothecin, BN 80915, irinotecan, DB 67, BNP 1350, exatecan, lurtotecan, ST 1481, and CKD 602. Other natural products include azathioprine; brequinar; phenoxizone biscyclopeptides, e.g. dactinomycin; basic glycopeptides, e.g. bleomycin; anthraquinone glycosides, e.g. plicamycin (mithrmycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like. Other chemotherapeutic agents include metal complexes, e.g. cisplatin (cis-DDP), carboplatin, etc.; ureas, e.g. hydroxyurea; and hydrazines, e.g. N-methylhydrazine. Retinoids, e.g. vitamin A, 13-cis-retinoic acid, trans-retinoic acid, isotretinoin, etc.; carotenoids, e.g. beta-carotene, vitamin D, etc.

Other combination therapies include administration with cell-specific antibodies or immunoregulatory antibodies such as checkpoint inhibitors, for example antibodies selective for tumor cell markers, radiation, surgery, and/or hormone deprivation (Kwon et al., Proc. Natl. Acad. Sci U.S.A., 96: 15074-9, 1999). A number of antibodies are currently in clinical use for the treatment of cancer, and others are in varying stages of clinical development. For example, anti-CD20 (rituximab); anti-CD52 (alemtuzumab); anti-CD22, etc. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer. Monoclonal antibodies that have been used in solid tumors include, without limitation, edrecolomab and trastuzumab (herceptin). Edrecolomab targets the 17-1A antigen seen in colon and rectal cancer. Trastuzumab targets the HER-2/neu antigen. Cetuximab (Erbitux) binds to the EGF receptor (EGFR), and has been used in the treatment of carcinomas.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—CH2-), ethylene (—CH2CH2-), propylene (—CH2CH2CH2-), 2-methylpropylene (—CH2-CH(CH3)—-CH2-), hexylene (—(CH2)6-) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, pi perazino, piperidino, tetrahydrofuranyl, etc.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO2), nitroso (—NO), sulfo (—SO2-OH), sulfonato (—SO2-O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO2-aryl), phosphono (—P(O)(OH)2), phosphonato (—P(O)(O—)2), phosphinato (—P(O)(O—)), phospho (—PO2), and phosphino (—PH2), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Methods of Use

Methods are provided for treating or reducing primary or metastatic cancer through inhibition of transcription factor pathways involved in proteasome expression. In particular, compositions and methods of use thereof are provided for inhibition of N-Glycanase1 (NGly1). Inhibition of NGly1 reduces proteasome expression. The NGly1 inhibitor may be used as a single agent, or in combination with an agent that directly inhibits proteasome activity. The combination of agents may provide for increased overall survival of an individual being treated for cancer. The combination of agents may provide for a synergistic benefit in killing of cancer cells, relative to administration as a single agent. Such methods include administering to a subject in need of treatment additional combinations with a chemotherapeutic drug, radiation therapy, etc.

In some embodiments an NGly1 inhibitor has a structure I, II or III, as described herein. In some embodiments the compound inhibits NGly1 and does not inhibit caspase activity. In some embodiments the inhibitor inhibits Ngly1 mechanistically by inhibiting nucleophilic attack of a cysteine residue at the amide linkage between the asparagine side chain of the target protein and the N-linked oligosaccharide. In some embodiments a pharmaceutical formulation is provided of an NGly1 inhibitor with a pharmaceutically acceptable excipient. In some embodiments the formulation is provided in a unit dose formulation, providing a dose effective to reduce proteasome expression in a targeted cell.

Compositions

Effective doses of an Ngly1 inhibitor for the treatment of cancer, alone or in combination with an effective dose of a direct proteasome inhibitor, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage of each agent may range from about 0.0001 to 100 mg/kg, for example from about 0.001, from about 0.01, from about 0.1 mg/kg; up to about 100 mg/kg, up to about 50 mg/kg, up to about 25 mg/kg, up to about 10 mg/kg. An exemplary treatment regime may provide administration once daily, once every other day, once every 3 days, once weekly, twice monthly, once monthly, etc., as well as times in between. Therapeutic entities of the present invention are usually administered on multiple occasions. Intervals between single dosages can be about daily, weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the agent in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor regrowth, tumor metastasis or tumor invasion of cancers. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Compositions may be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising an Ngly1 inhibitor and instructions for use. The NGly1 inhibitor may be provided in a unit dose formulation with a pharmaceutically acceptable carrier. The kit can further contain a least one additional reagent, e.g. an effective dose of a direct proteasome inhibitor, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXPERIMENTAL

Example 1

A potential limitation of the effectiveness of proteasome inhibitors is found in the mode of action of the transcription factor Nuclear Factor, Erythroid 2 Like 1 (NFE2L1, also called Nrf1). Nrf1 is a member of the "cap'n'collar" bZIP transcription factor family and is a master regulator of many vital metabolic pathways, such as lipid and amino acid metabolism, the transactivation of antioxidant enzymes, bone formation, and the maintenance of proteostasis. Importantly, Nrf1 is the sole regulator of proteasomal subunit gene expression. Thus, Nrf1 is essential for viability and cell survival.

A unique feature of Nrf1 is its own complex regulation. Uncommon for transcription factors, Nrf1 contains multiple N-glycosylation sites and its activation proceeds via the endoplasmic reticulum-associated degradation (ERAD) pathway. Beginning its tenure as a misfolded and N-glycosylated protein in the ER, Nrf1 is retro-translocated from the ER to the cytosol where it is de-N-glycosylated and partially proteolytically processed by the aspartyl protease DNA-damage inducible 1 homolog 2 (DDI2). The now active p110 form of Nrf1 is able to translocate to the nucleus and activate proteasomal subunit gene expression.

Under conditions of normal proteostasis, Nrf1 is continually targeted for proteasomal degradation by retro-translocation through the VCP/p97 complex. The protein is thereby maintained at low levels under basal conditions. However, under conditions of a compromised proteasome such as treatment with proteasome inhibitors, de-N-glycosylated Nrf1 accumulates and exerts its nuclear functions, including transactivation of proteasomal subunit genes. Thus, Nrf1 is thought to mediate a "bounce-back" response that sustains proteasomes at levels that maintain proteostasis. This mode of action can counteract the effective inhibition of the proteasome by small molecules in cancer therapy. Inhibiting Nrf1 could significantly improve the effectiveness of small molecule proteasome inhibitors. Nrf1 itself is not a viable target for inhibitors, due to its complex processing and constant degradation. Interfering in the activation pathway of Nrf1, however, provide a promising approach to potentiate proteasome inhibition for cancer treatment.

The de-N-glycosylation of Nrf1 is likely to be important for its function. Analysis of the protein's sequence shows a complex domain architecture comprising an N-glycosylated "NST" domain with 7 potential N-glycosites that is flanked on either side by acidic domains (AD1 and 2). It has been speculated that deglycosylation of the NST domain, with concomitant conversion of Asn to acidic Asp residues, would create a functional transactivating domain (TAD) required for transcriptional activation. Indeed, mutation of Nrf1's potential N-glycosites from Asn to Asp enhanced its ability to activate transcription using a luciferase reporter gene construct.

This observation, combined with the finding that Nrf1 activation involves processing from a 120 MW species to a deglycosylated 110 MW species upon proteasome inhibition, suggested that de-N-glycosylation activity is required for optimal Nrf1 function.

The enzyme responsible for N-glycan removal in the cytosol is N-Glycanase1 (NGly1). It is shown herein that NGly1, is involved in the processing of Nrf1 and in particular is important for its activation. NGly1 is a potent target for small molecule inhibitors, which can prevent the activation of Nrf1 and thereby potentiate cancer therapies based on proteasome inhibitors by disrupting proteasome bounce-back pathways of Nrf1. A combination of NGly1 inhibitors and proteasome inhibitors provides a more effective strategy for cancer treatment than proteasome inhibitors alone.

Results and Discussion:

We propose that NGly1 plays a central in the processing and activation of the transcription factor Nrf1. FIG. 1A illustrates a proposed Nrf1 activation pathway including the necessary step of de-N-glycosylation by the enzyme NGly1. Nrf1 was investigate in the presence and absence of NGly1. Mouse embryonic fibroblasts (MEFs) derived from NGly1$^{-/-}$ mice (Tadashi Suzuki, Riken, Japan) were treated with the proteasome inhibitor carfilzomib (FIG. 1B) and compared to Wt MEFs that were treated under equal conditions. Immunoblot analysis revealed an abnormal Nrf1 processing in NGly1 cells after treatment with carfilzomib (FIG. 10).

In a second attempt, we used Nrf1 overexpressing HEK cells and applied the small molecule Z-VAD-fmk (FIG. 1B) to inhibit NGly1 before treating the cells with carfilzomib. Z-VAD-fmk has been shown to inhibit caspases as well, thus we used the potent pan-caspase inhibitor Q-VD-OPh, which does not act on NGly1, as a control molecule. Cells treated with Z-VAD-fmk showed abnormal processing of Nrf1, especially in presence of carfilzomib. The higher abundance of the p120 band indicates the existence of the N-glycosylated form of Nrf1 as the main species in cells treated with Z-VAD-fmk. In contrast, cells treated with Q-VD-OPh showed a similar processing of Nrf1 compared to untreated cells, with de-N-glycolysated Nrf1 (p110 band) as the predominant species after incubation with carfilzomib (FIG. 10). Thus, the incorrect processing of Nrf1 that we observed in cells treated with Z-VAD-fmk results from inhibition of NGly1 and not from caspase inhibition. Both experiments reveal that functional NGly1 is required for de-N-glycosylation and hence the correct processing of Nfr1.

Knowing that NGly1 is involved in the processing of Nfr1 it was determined whether de-N-glycosylation is required for activating the transcription factor and hence the production of proteasomal subunits. According to the theory the active form (p110) of Nrf1 that translocates to the nucleus and activates proteasome genes, is produced upon removal of the N-glycans. Using a construct in which three copies of the antioxidant respond element (ARE) of the human PSMA4 gene were inserted upstream of a SV40 promoter that drives the expression of firefly luciferase in a dual luciferase reporter assay, where plasmids expressing renilla luciferase were used as internal transfection control, we compared the reporter activity in NGly1$^{-/-}$ MEFs and Wt MEFs after treatment with carfilzomib. Wt cells showed an increase in PSM activity after 12 hour of incubation with carfilzomib whereas the NGly1$^{-/-}$ cells showed no response to the proteasome inhibitor treatment (FIG. 2A).

We conclude that NGly1$^{-/-}$ cells lack the active form of Nrf1 and hence cannot respond with bounce back reaction to proteasome inhibition. The same experiment was performed in Nrf1 overexpressing HEK cells in which NGly1 was inhibited by Z-VAD-fmk prior to incubation with carfilzomib. The caspase inhibitor QVD-OPh served as control to out rule that observed effect resulted from caspase inhibition. Only cells incubated with Z-VAD-fmk did not show an increased reporter activity indicating that active Nrf1 was lacking in those cells due to inhibition of NGly1 (FIG. 2B).

We further used confocal microscopy to visualize the localization of Nrf1 in MEFs and Nrf1 overexpressing HEK cells before and after treatment with carfilzomib (FIGS. 2B and C). In absence of carfilzomib Wt and NGly1$^{-/-}$ MEFs show Nrf1 (in white) in low abundance and mainly in the cytosol (FIG. 2B). After treating the cells with carfilzomib for several hours, wt MEFs show Nrf1 in the nucleus whereas NGly1$^{-/-}$ MEFs only show a higher abundance of Nrf1 in the cytosol. The same effect was observed in the Nrf1 overexpressing HEK cells (FIG. 2C), but even more severely due to the higher abundance of Nrf1 in those cells. Untreated cells show Nrf1 mainly in the cytosol around the ER. After incubation with carfilzomib the majority of Nrf1 was observed in the nucleus. Cells treated with Z-VAD-fmk prior to incubation with carfilzomib showed a high abundance of Nrf1 in the cytosol. Incubation with the control molecule QVD-OPh gave similar results to non-treated cells confirming that the effect observed in cells treated with Z-VAD-fmk is a result of NGly1 rather than caspase inhibition. These results clearly show the link between NGly1 and Nrf1. Taking all the results in account we conclude that functioning NGly1 is required to activate Nrf1.

With evidence that Nrf1 is processed incorrectly with non-functioning NGly1, we sought to determine a link between NGly1 and the proteasome. To confirm that a lack of NGly1 would increase susceptibility to proteasome inhibition due to a lack of functional Nrf1 as the main regulator for proteasome subunit production, MEF NGly1$^{-/-}$ cells were compared to MEF WT with increasing amounts of carfilzomib (FIG. 3A). After 24 h incubation, NGly1$^{-/-}$ cells were found to be over 2-fold more sensitive to treatment with carfilzomib at doses ranging from 5-100 nM. The same effect could be observed at 4 h, albeit to a lesser extent. The lag time for activation of proteasomal subunit bounce back, which has been shown to take roughly 8 hours, could explain the decreased effect of NGly1 KO at early time points.

To account for the possibility that a small amount of NGly1 could be as functional in the cell as the normal amount, K562 cells were treated with dCAS9 and a sgRNA corresponding to Nrf1, NGly1, or a control sequence, then measured for survival in the presence of increasing concentrations of carfilzomib (FIG. 3b). With no sgRNA or with a control sgRNA, the LD$_{50}$ of carfilzomib was found to be 40 nM (FIG. 3c). In the dCAS9 knockdowns of Nrf1 or NGly1 (sgNrf1-A, sgNrf1-B, and sgNGly1), the LD$_{50}$ was effectively shifted lower by about 2-fold to 20 nM for each case. This implies that knockdown of NGly1 has a very similar effect to knockdown of Nrf1, and that cells lacking the normal amount of these proteins are further compromised to proteasome inhibition.

Considering the effect of NGly1 KO or knockdown for proteasome inhibitor potentiation, we hoped to find the same effect through the use of a small molecule inhibitor of NGly1. Attempts to use Z-VAD-fmk to potentiate proteasome inhibition in multiple myeloma cell lines were unsuccessful, possibly due to its activity as a potent pan-caspase inhibitor.

To rectify this problem, we set out to find a novel inhibitor of NGly1. The mechanism of NGly1 is nucleophilic attack of a cysteine residue at the amide linkage between the asparagine side chain of the target protein and the N-linked oligosaccharide. This mechanism, similar to the cysteine protease character of the caspases, explains the cross-reactivity of the electrophilic fluoromethylketone group of Z-VAD-fmk between the caspases and NGly1. We hypothesized that this nucleophilic sulfur-based mechanism could be utilized to perform a targeted screen of a small library of compounds designed to react with cysteine proteases.

Figure 4B:
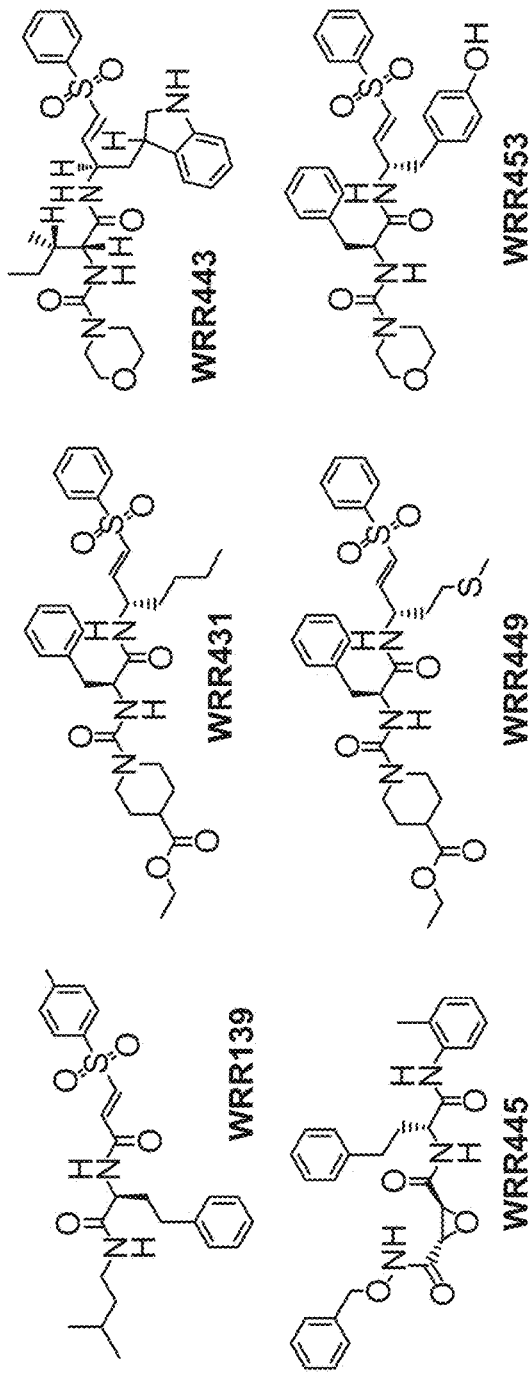
Figure 4C:
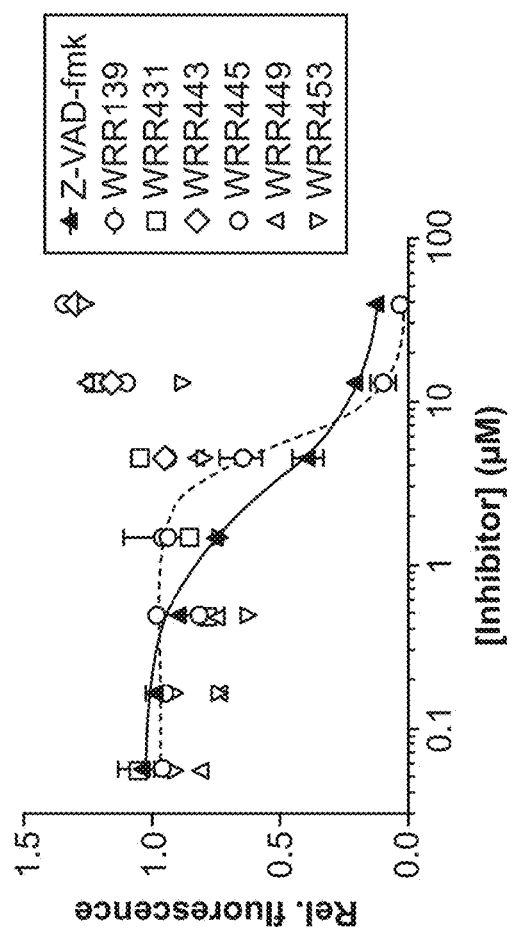

The assay used was a modified version of the fluorimetric assay first described by the Cresswell lab in 2011. Prepared by the Steinmetz lab, a stably transfected K562 cell line was used. Mutated to misfold and contain a site for N-glycosylation, the expressed ddVenus would only properly fold, and thus fluoresce, upon deglycosylation by NGly1 and concurrent conversion of the glycosylated asparagine residue to aspartic acid (FIG. 4A). Thus inhibition of NGly1 would not activate fluorescence in this assay. With this method a library of about 600 cysteine-protease inhibitor-like compounds were screened. Six hits were found, all of which were peptide-derived structures with an electrophilic warhead consisting of either a vinyl sulfone or epoxyketone (FIG. 4B). Stocks of these compounds were used to validate their efficacy in the Cresswell assay, and the compound WRR139 was the only compound found to effectively reduce fluorescence with an IC$_{50}$ of 5.5 µM (FIG. 4C). For comparison, Z-VAD-fmk was found to have an IC$_{50}$ of 4.4 µM in the same assay.

Figure 4D:
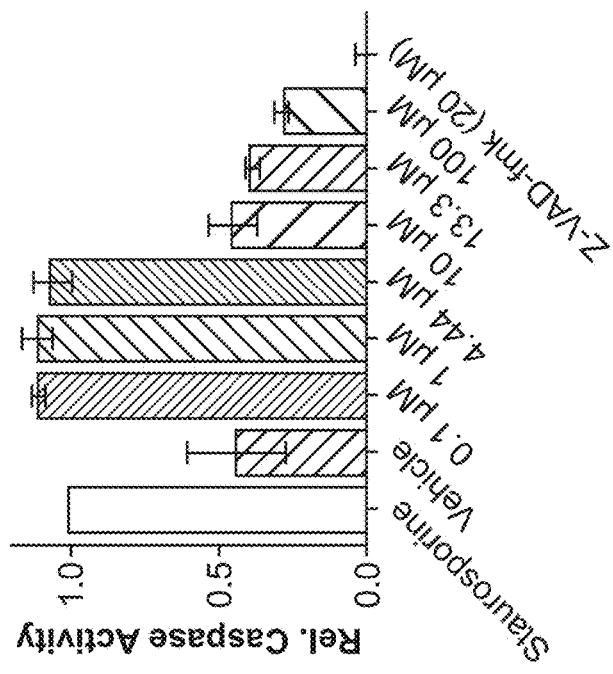

To detect direct inhibition of NGly1 by WRR139, the mass shift of RNAse B exposed to recombinant Ngly1 was observed by gel electrophoresis. In the presence of Ngly1, RNAse B was fully converted from its glycosylated band at pXXX to a deglycosylated protein at pXXX (FIG. 4D). In the presence of Z-VAD-fmk or WRR139, only the original band remains, with no conversion to the deglycosylated form.

Figure 5A:
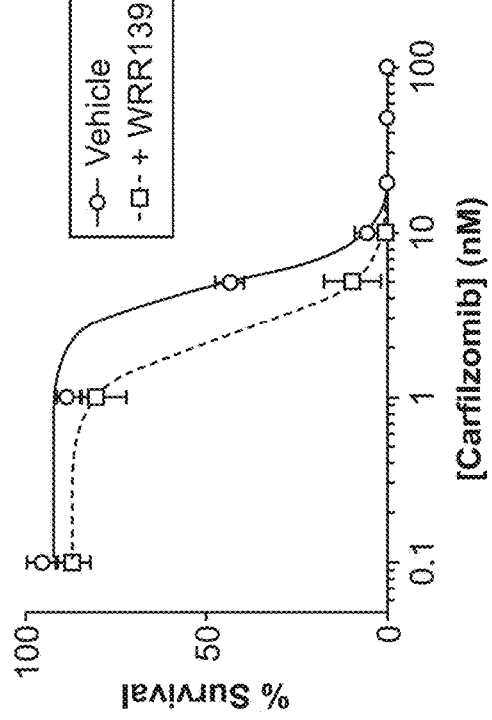
FIG. 5A-5C. Inhibition of NGly1 potentiates treatment of multiple myeloma by proteasome inhibition.
Figure 5B:
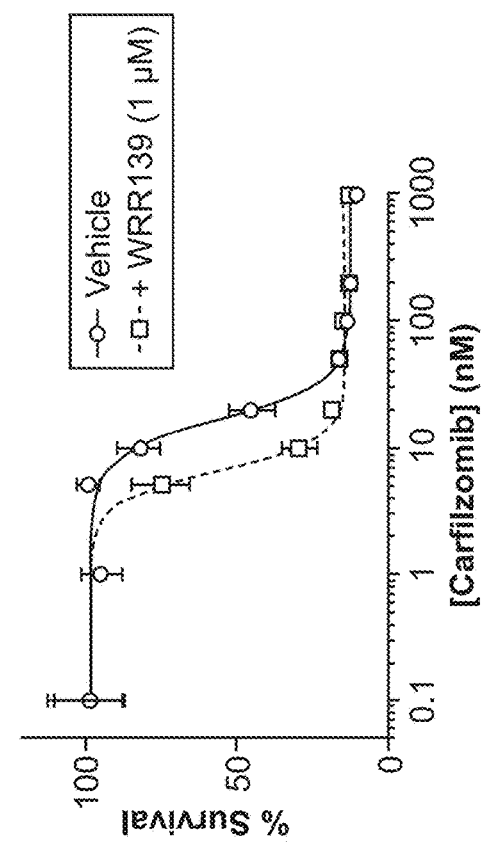
Figure 5C:
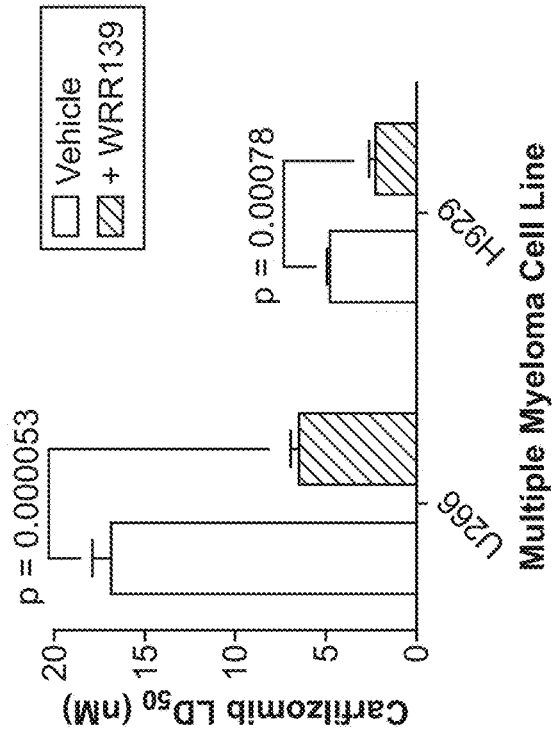

We were further interested to see whether this molecule would also hit caspases, similar to the known Ngly1 inhibitor Z-VAD-fmk. To confirm that WRR139 did not also inhibit caspases 3/7 at the range in which it inhibits Ngly1, a range of concentrations was tested for inhibition against caspases 3/7. Inhibition of caspases 3/7 was not observed until a concentration of about 10 µM was reached. In addition, the relative activity was not lowered below the range observed by induced apoptosis With an Ngly1 inhibitor in hand that did not inhibit apoptosis, we tested if small molecule inhibition of Ngly1 could potentiate proteasome inhibition in MM cell lines. In U266 and H929 cell lines, co-inhibition with WRR139 and carfilzomib significantly decreased cell survival after 24 hours compared to carfilzomib alone (FIGS. 5A and 5B). This reduction in survival represented a 2.6 fold and 2 fold increase in killing in U266 and H929, respectively (FIG. 5C). These results demonstrate that deactivating Nrf1 via the inhibition of Ngly1 potentiates the effectiveness of proteasome inhibitors. Interestingly, the U266 cell line is considered to be a cell line resistant to proteasome inhibition compared to other MM lines, such as H929. The greater increase in efficacy of the combined treatment in cells considered resistant to proteasome inhibition provides for a useful combination therapy.

In summary, we have investigated new avenues to potentiate the effectiveness of proteasome inhibitors that are currently applied as treatment for certain cancer types such as multiple myeloma. We showed that deactivation of the main regulator of proteasome subunits, the transcription factor Nrf1, can result in a higher potency of small-molecule proteasome inhibitors. Since Nrf1 itself is a poor target for inhibitors we inhibited an enzyme involved in the processing of Nrf1, that is NGly1.

In initial experiments, investigating processing, activation and localization of Nrf1 we were able to prove the link between NGly1 and Nrf1 and showed that de-N-glycosylation by this enzyme is required to produce the active form of Nrf1. A higher sensitivity of cells lacking NGly1 towards proteasome inhibitors and a reduced activation of proteasome genes compared to wt cells revealed the link between NGly1 and the proteasome and accordingly a reduced bounce back reaction in cells with non-functioning NGly1. Based on these findings we scanned a library of cysteine-protease inhibitor-like compounds using a ddVenus fluorescence assay that would show activity upon deglycosylation, in order to find molecules inhibiting NGly1. Six peptide-derived structures with an electrophilic warhead consisting of either a vinyl sulfone or epoxyketone were identified as hit compounds and were further investigated. WRR139 showed the highest efficiency in inhibiting NGly1 in K562 cells with an I0$_{50}$ higher that the existing NGly1 inhibitor Z-VAD-fmk, which furthermore also inhibits caspases. Inhibition of NGly1 was further validated by a gel shift assay using RNAse B exposed to the purified recombinant enzyme in presence or absence of WRR139. In addition, we found that caspases 3/7 were not inhibited in the concentration range of WRR139 that is required to effectively inhibit NGly1. Caspases were hit at significantly higher concentrations. Taken into account that caspase inhibition avoids apoptosis in cells this result clearly shows the benefit of WRR139 compared to Z-VAD-fmk.

Finally, we used two multiple myeloma cells lines to test whether the combination of our NGly1 inhibitor WRR139 and the proteasome inhibitor carfilzomib could potentiate the effectiveness in comparison to proteasome inhibition alone. Preliminary results showing a significant reduced cell survival for the coinhibition of both compounds compared to carfilzomib alone confirmed our initial theory. Interestingly, this strategy showed also success for the MM cell line that is resistant against proteasome inhibition. We believe that our approach and the here discussed findings hold great potential for the treatment of relapsed multiple myeloma as well as other cancer types.

Materials and Methods

Cell culture. Primary MEFs derived from knockout animals and immortalized using SV40 (a kind gift from Tadashi Suzuki, RIKEN, Japan) were grown in Dulbecco's modified Eagle's medium (DMEM) supplemented with 10% fetal bovine serum (Clontech Laboratories), penicillin, and streptomycin (Fisher Scientific) at 37° C. in 5% $CO_2$.

Nrf-3× Flag overexpressing HEK cells (RDB-2867; a kind gift from Senthil Radhakrishnan, Virginia Commonwealth University) were obtained by cloning Human Nrf1 coding region along with a C-terminal 3× Flag sequence into pcDNA3.1+ (Invitrogen, Carlsbad, Calif.). Cells were grown in Dulbecco's modified Eagle's medium (DMEM) supplemented with 10% fetal bovine serum (Clontech Laboratories), penicillin, and streptomycin (Fisher Scientific) at 37° C. in 5% CO2.

K562 cells were grown in Iscove's Modified Dulbecco's Medium (IMDM) supplemented with 10% fetal bovine serum (Clontech Laboratories), penicillin, and streptomycin (Fisher Scientific) at 37° C. in 5% CO2.

U266 cells were grown in RPMI-1640 supplemented with 15% fetal bovine serum (Clontech Laboratories), penicillin, and streptomycin (Fisher Scientific) at 37° C. in 5% CO2.

H929 cells were grown in RPMI-1640 supplemented with 10% fetal bovine serum (Clontech Laboratories), penicillin, and streptomycin (Fisher Scientific) and 50 mM BME beta-mercaptoethanol (BME) at 37° C. in 5% CO2.

Immunoblot Analysis. Cells were lysed in RIPA buffer (50 mM Tris [pH 7.4], 150 mM NaCl, 1% NP40, 1% Na. Deoxycholate, 0.1% SDS, and 1 mM EDTA) supplemented with protease and phosphatase inhibitor cocktail (Pierce). For detecting Nrf1 a rabbit monoclonal antibody raised against the N terminus (D5B10, Cell Signaling) was used. Other immunoblots were performed with antibodies specific for Flag tag (Sigma-Aldrich) and β-actin (Cell Signaling).

Luciferase Assays. The construct 3xPSMA4-ARE-Luc (RDB-2415; a kind gift from Senthil Radhakrishnan, Virginia Commonwealth University) was described previously. Briefly, an oligo (5'-cgagccgtgggcacga TGACTCTGCA ccgcctcctctgagccgtgggcacga TGACTCTGCA ccgcctcctct-gagccgtgggcacga TGACTCTGCA ccgcctcctctg-3') (SEQ ID NO: 10) containing three copies of a putative ARE (shown in uppercase) derived from the first intron of the human PSMA4 gene was annealed to its corresponding reverse-complement oligo and cloned into pGL3-promoter vector (Promega). The promoter reporter was generated by inserting this construct upstream of a minimal SV40 promoter, driving the expression of a firefly luciferase.

Cells were transiently transfected with the firefly (promoter reporters) and renilla luciferase (pRL-TK; Promega) constructs along with effector plasmid as required. Cells were treated with with compoubds or vehicle control for 12 hours. Afterwards cells were lysed in the luciferase assays were performed using the dual luciferase reporter assay system (E1910; Promega) according to the instructions from the manufacturer. The firefly luciferase activity was normalized to renilla luciferase activity for all experiments.

Cell Viability Assays. Cells were treated in 96-well plates with proteasome inhibitors in concentrations ranging from 1 to 100 μg/ml for 4 or 24 h respectively. WST-1 reagent was obtained from Roche (Germany) and used according to manufacturer instructions. Read-out was performed by measuring the absorbance at 450 nm using a Spectra max®i3x (VWR, Australia) plate reader.

Immunofluorescence followed by confocal imaging. MEFs and Nrf-3× Flag overexpressing HEK cells were grown to 80% confluency on cover slips. Cells were treated with NGLy1-, caspase-, and proteasome inhibitors as indicated and allowed to recover in fresh media for one hour before cells were fixed using 100% ice cold methanol. Cells were treated with a primary rabbit monoclonal antibody raised against the N-terminus of Nrf1 (D5B10, Cell Signaling) and a secondary polyclonal Alexa Fluor0647 AffiniPure Fab Fragment Goat Anti-Rabbit IgG (H+L) (Jackson Immuno Research). After washing with PBS cover slips were treated with ProLong®Diamond Antifade Mountant (P3697, Thermo Fischer) containing 49,6-Diamidino-2-Phenylindole (DAPI) for nuclear DNA staining, placed on slides and dried overnight. Thereafter, subcellular location of Nrf1 (far-red channel) was examined by confocal imaging using a Nikon Eclipse Ti and a 60× magnification. Images were analyzed using Imaris analysis software (version). Bar=10 mm.

Screen of ~600 compounds with the Cresswell Assay. Screens were performed clear, V-bottom 96-well plates. Plates were prepared with negative control 2 μL DMSO (A1) and positive control 1 μL DMSO+1 μL 10 mM Z-VAD-fmk (final conc. 100 uM Z-VAD-fmk; A12-H12). Wells A2-A11 contained 1 μL DMSO, the remaining wells contained 1 μL of 1 mM stocks of compounds from the library.

100 μL of suspended K562 ddVenus cells were added to the plate at 1×10^6 cells/mL. Wells A1-A12 contained cells in growth media. The remaining wells contained cells in growth media supplemented 100 uM carfilzomib.

Plates were incubated for 6 hours at 37° C. with 5% $CO_2$ and subsequently analyzed by automated flow cytometry using a (instrument details), with cutoffs at 50 uL and 50,000 events. The mean of fluorescence in FL1 was plotted for each well.

Wells that showed decreased fluorescence of 3 standard deviations below the mean of the positive control (maximum fluorescence) were identified at hits. Z-factor for the assay ranged between 0.38-0.85.

Cell survival with proteasome inhibitor. Cell survival experiments using the Cell Titer-Glo 2.0 assay were performed in opaque white flat-bottomed 96-well plates. The cells (1.0-2.0×10$^4$ in 100 μL fresh media) were treated under the desired conditions and incubated for 24 or 48 h before addition of 100 μL assay reagent. Viability was calculated as percent signal compared to vehicle treated cells. Regression analysis and $IC_{50}$ calculations were performed with GraphPad Prism 7.0.

U266 and H929: U266 or H929 cells were seeded at a density of 0.1 million cells/mL in RPMI medium (100 μL per well). The following day, carfilzomib, DMSO, or WRR139 were added in DMSO to final concentrations as shown for a maximum final concentration of 1% DMSO (v/v). After 48 h of incubation at 37° C. with 5% $CO_2$, the plate was retrieved and treated with the Cell Titer-Glo 2.0 assay. After 10 minutes incubation the plate was analyzed by measuring the luminescence using a Spectra max®i3x (VWR, Australia) plate reader.

K562: K562 cells(WT or NGLY1$^{-/-}$) were seeded at a density of 0.2 million cells/mL in RPMI medium 100 µL per well. The following day, carfilzomib or DMSO was added to final concentrations as shown for a maximum final concentration of 0.2% DMSO (v/v). After 24 h of incubation at 37° C. with 5% $CO_2$, the plate was retrieved and treated with the Cell Titer-Glo 2.0 assay. After 10 minutes incubation the plate was analyzed by measuring the luminescence using a Spectra max®i3x (VWR, Australia) plate reader.

Caspase 3/7 inhibition assay. 1 million U266 cells were suspended in 10 mL RPMI 15% BSA+PS, and plated into a flat-bottom, white-walled 96-well plate (100 µL per well). The plate was incubated at 37° C. overnight. The following day, cells were treated with staurosporine (apoptosis inducer, final concentration 1 µM), WRR139 or Z-VAD-fmk (at final concentrations shown) or DMSO to a final concentration of 2% DMSO (v/v) respectively. The plate was incubated for 8 hours at 37° C. Caspase-Glo kit reagent (company details) was prepared as per instruction from the manufacturer and after equilibration to 23° C. 100,ml of the reagent was added to each well. The plate was incubated at room temperature for 60 minutes and subsequently analyzed by measuring the luminescence using a Spectra max®i3x (VWR, Australia) plate reader. Caspase inhibition was calculated by subtracting background (signal from media containing no cells) and comparison to signal from cells with induced apoptosis (staurosporine only).

Generation of CRISPRi-mediated knockdown k562 cell lines: The CRISPRi K562 cell line that stably expresses dCas9-KRAB[1] and the third-generation lentiviral system were obtained from the group of Jonathan Weissman (University of California, San Francisco). The generation of CRISPRi-based knockdown K562 cell lines was carried out according to the published procedure. First, protospacer sequences with the highest predicted CRISPRi activity scores reported by Horlbeck et al. were cloned into the previously described sgRNA-expressing lentiviral transfer plasmid. An sgRNA construct targeting yeast GAL4-UAS was used as negative control, as previously described. The lentivirus was generated in HEK293T cells using a third-generation lentiviral plasmid system.

For lentiviral infection, K562 cells were first seeded at a density of 0.1 million/ml in a 24-well plate overnight. The next day, lentivirus carrying individual sgRNA vector was add to each well. The plate was centrifuged at 1,000×g at 33° C. for thirty minutes, and then returned to normal cell culture incubation condition. Two days after infection, puromycin was added to a final concentration of 1.25 µg/ml, and the selection was continued for 4 days. All experiments performed on the sgRNA-transduced cells were then carried out with no more than ten passages after the puromycin selection.

To determine the level of gene knockdown, 0.2 million of cells were collected from each K562 cell line, and RNA was extracted by the Quick-RNA™ MicroPrep kit (Zymo Research, CA, USA), according to the manufacturer's instruction. 200 ng of the extracted RNA was reversed transcribed to cDNA using the ProtoScript® II First Strand cDNA Synthesis Kit (New England Biolabs, MA, USA) with the supplied Oligo d(T)23 VN primer, according to the manufacturer's instruction. Quantitative PCR reactions were prepared using the SYBR® Green PCR Master Mix (Thermo Fisher Scientific), according to the manufacturer's instruction. PCR reactions were carried out in a CFX96 Touch™ Real-Time PCR Detection System (Bio-Rad, CA, USA).

Sequence of protospacers of each sgRNA construct:

```
NFE2L1 (Nrf1):
                                       (SEQ ID NO: 1)
5'-GAAGCTCCGGCGCCGAGAGT-3'

NGLY1:
                                       (SEQ ID NO: 2)
5'-GTGAGGCGCCTGCTCAGTGT-3'

GAL4-4:
                                       (SEQ ID NO: 3)
5'-GAACGACTAGTTAGGCGTGTA-3'
```

Primer sequences for quantitative PCR:

```
GAPDH:
                                       (SEQ ID NO: 4)
FW:       5'-GGTGGTCTCCTCTGACTTCAACA-3'

(SEQ ID NO: 5)
RV:       5'-GTTGCTGTAGCCAAATTCGTTGT3'

NFE2L1:
                                       (SEQ ID NO: 6)
FW:       5'-AGTGGCAAGATCTCATGTCC-3'

(SEQ ID NO: 7)
RV:       5'-GCTGAAGAGTAAGAAGTCCTGG-3'

NGLY1:
                                       (SEQ ID NO: 8)
FW:       5'-AATATCTGGGTCAGTGGCTTG-3'

(SEQ ID NO: 9)
RV:       5'-CATTTTCCACACGCCATTCTC-3'
```

Carfilzomib sensitivity of CRISPRi-knockdown k562 cell lines. Carfilzomib dissolved in DMSO at a concentration of 10 mM was used freshly or stored at −80° C. for no longer than a month without repeated freeze-thaw cycles. K562 cells were seeded at a density of 0.2 million cells/ml in 100 µl of RPMI medium in each well of a 96-well plate for 18 hours before treatment. The next day, serial-diluted Carfilzomib or DMSO was added to the cells with a final concentration of DMSO of 0.1% (v/v) in each well. After 48 hours of incubation at 37° C., the plate was retrieved and stained with a calcein-based LIVE/DEAD® Viability/Cytotoxicity Kit (Thermo Fisher Scientific), according to the manufacturer's instruction. The cells were then counted on an Accuri C6 flow cytometer (BD Biosciences, CA, USA). A total of 10,000 events was collected for each well. The viability was calculated as the percent of calcein-positive cells in each Carfilzomib-treated sample, normalized to that of the DMSO-treated vehicle control.

Synthesis

Compound 2

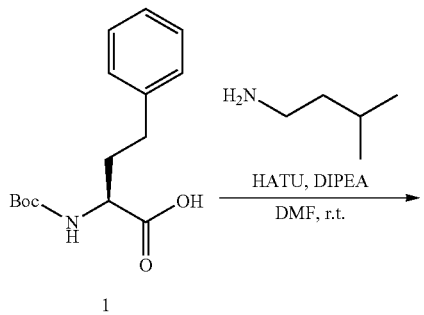

1

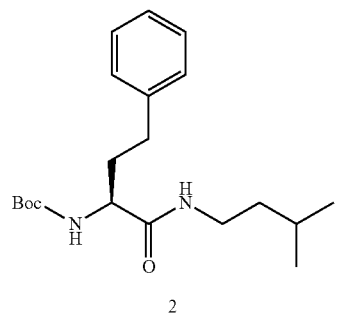

2

Experimental: Boc-Homophenylalanine 1 (500 mg, 1.78 mmol) was dissolved in 8 mL DMF. To this solution was added HATU (741 mg, 3.56 mmol) and DIPEA (929 μL, 5.34 mmol) in succession. The resulting mixture was stirred for 30 minutes before addition of isopentylamine (412 μL, 3.56 mmol). The solution quickly turned yellow and the mixture was allowed to stir for 14 h. The mixture was diluted with EtOAc (30 mL), washed with water (2×20 mL), sat. NaHCO₃ (2×20 mL), and brine (20 mL). The organic layer was collected, dried over MgSO₄, and filtered. The clear yellow solution was concentrated under reduced pressure, and the yellow residue was purified by column chromatography (2:1 Hexanes/EtOAc). The product 2 was isolated as a clear, colorless foam (365 mg, 58% yield). $^1$H NMR (300 MHz, Chloroform-d) δ 7.30-7.12 (m, 6H), 6.78 (s, 1H), 5.59 (d, J=7.9 Hz, 1H), 4.26-4.14 (m, 1H), 3.22 (s, 2H), 2.74-2.62 (m, 2H), 2.01-1.90 (m, 1H), 1.62 (dt, J=13.2, 6.7 Hz, 1H), 1.47 (s, 14H), 1.12 (s, 1H), 0.91 (d, J=6.6 Hz, 6H). $^{13}$C NMR (126 MHz, CDCl₃) δ 172.18, 156.10, 141.36, 128.70, 128.62, 126.29, 80.10, 77.63, 77.37, 77.12, 54.42, 38.61, 38.01, 34.67, 32.18, 28.61, 26.02, 22.72, 22.67. HRMS (ESI) m/z: calculated. R$_f$: 0.47 (2:1 Hexanes/EtOAc).

Compound 3

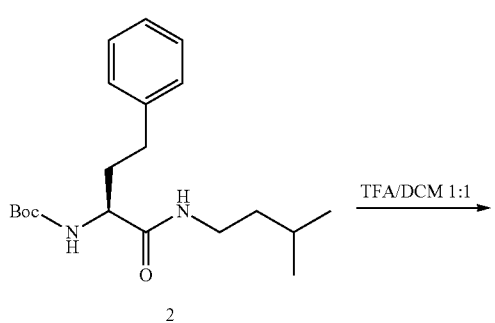

2

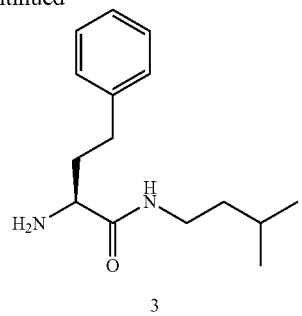

3

Experimental: Compound 2 (360 mg, 1.03 mmol) was dissolved in DCM (10 mL) with stirring, and TFA (10 mL) was added to the solution. The mixture was stirred until complete disappearance of the starting material by TLC (2:1 Hexanes/EtOAc, ~20 min). The solvent was removed under reduced pressure, and the residue was dissolved in DCM (20 mL) and washed with saturated NaHCO₃ (3×15 mL). The combined aqueous layers were back extracted with DCM (2×20 mL). The combined organic layer was dried over MgSO₄, filtered, and concentrated under reduced pressure. The resulting yellow oil was found to be compound 3 and was used without further purification (247.9 mg, 97%). $^1$H NMR (400 MHz, Chloroform-d) δ 7.29 (d, J=7.6 Hz, 1H), 7.24-7.13 (m, 4H), 3.37 (dd, J=8.4, 3.9 Hz, 1H), 3.27 (q, J=6.8 Hz, 2H), 2.78-2.67 (m, 2H), 2.26-2.13 (m, 1H), 1.88-1.75 (m, 1H), 1.60 (s, 4H), 1.40 (q, J=7.5 Hz, 2H), 0.92 (d, J=6.6 Hz, 6H).

Compound 4

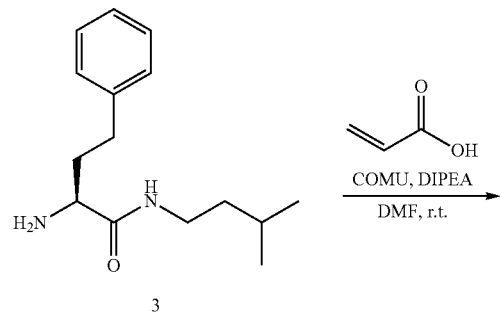

3

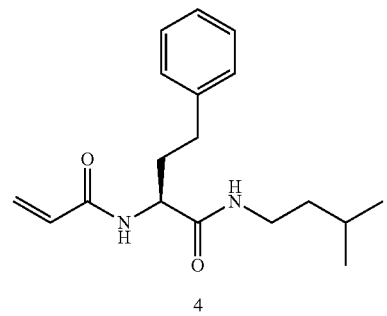

4

Experimental: Compound 3 (50 mg, 0.20 mmol) was dissolved in DMF (2.0 mL), and to this the acrylic acid (13.7 μL, 0.20 mmol) and DIPEA (104 μL, 0.60 mmol) were added with stirring. The mixture was cooled to 0° C. and COMU (86 mg, 0.20 mmol) was added. The flask was backfilled with N₂ and allowed to stir for 1 h. At this time the mixture was warmed to room temperature and stirred for another 3 hours. The mixture was diluted with EtOAc (10 mL) and washed with 1 N HCl (10 mL), sat. NaHCO$_3$ (2×10 mL), and brine (10 mL). The organic layer was dried over MgSO$_4$, filtered, and the solvent was removed under reduced pressure. The yellow residue was purified by column chromatography (2:1 to 3:2 to 1:1 Hexanes/EtOAc). The product 4 was isolated as a white powder (34.3 mg, 57%). $^1$H NMR (400 MHz, Chloroform-d) δ 7.23 (dd, J=13.5, 6.5 Hz, 1H), 7.14 (dd, J=19.9, 6.8 Hz, 4H), 6.85 (d, J=4.6 Hz, 1H), 6.32-6.11 (m, 2H), 5.64 (d, J=9.9 Hz, 1H), 4.63 (q, J=7.3 Hz, 1H), 3.34-3.26 (m, 1H), 3.19 (dt, J=13.1, 6.5 Hz, 1H), 2.67 (t, J=8.0 Hz, 2H), 2.16 (dq, J=14.6, 8.1 Hz, 1H), 2.04 (dt, J=13.9, 7.2 Hz, 1H), 1.60 (dt, J=13.2, 6.8 Hz, 1H), 1.39 (q, J=7.2 Hz, 2H), 0.89 (d, J=6.6 Hz, 5H). $^{13}$C NMR (101 MHz, CDCl$_3$) δ 171.73, 165.75, 141.20, 130.78, 128.70, 128.58, 127.11, 126.30, 77.59, 77.27, 76.95, 53.29, 38.48, 38.16, 34.60, 32.11, 26.05, 22.70, 22.61. HRMS (ESI) m/z: calculated. R$_f$ 0.4 (1:1 Hexanes/EtOAc).

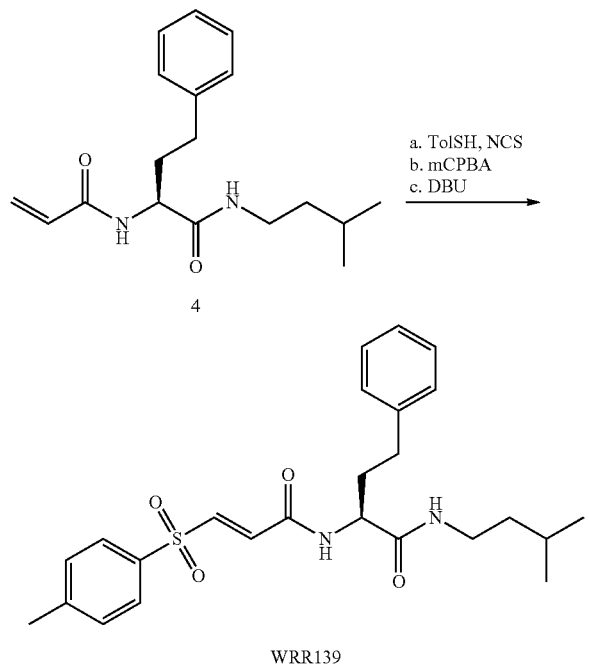

Experimental:

Addition: N-chlorosuccinimide (32.3 mg, 0.242 mmol) was dissolved in DCM (3 mL), and p-methylbenzenethiol (28.6 mg, 0.231 mmol) was added slowly with stirring. The solution turned orange and a precipitate formed. The mixture was allowed to stir for 30 minutes. Compound 4 was separately dissolved in DCM (0.25 mL) and added slowly. The reaction mixture was stirred for 14 h, then diluted with DCM (10 mL), washed with water (10 mL), and finally brine (10 mL). The organic phase was dried over MgSO$_4$, filtered, and concentrated under reduced pressure. The crude residue was used in the subsequent step without purification.

Oxidation: The crude residue obtained from the addition was dissolved in DCM (4 mL) and the solution was cooled to 0° C. The mCPBA (113 mg, 0.508 mmol) was added slowly, and the reaction was allowed to warm to r.t. and stirred. The reaction was monitored by TLC (the intermediate sulfoxide can be seen during this transformation, very polar), and after 1 h a second equivalent of mCPBA (113 mg, 0.508 mmol) was added due to incomplete conversion. The reaction mixture was stirred for 1 h before being quenched with sat. sodium thiosulfate (5 mL). The mixture was diluted with DCM (10 mL), and the organic layer was separated and washed with sat. NaHCO$_3$ (10 mL) and brine (10 mL). The organic phase was dried over MgSO$_4$, filtered, and concentrated under reduced pressure. After thorough drying under high vacuum, the chunky white residue was used directly in the subsequent step without purification.

Elimination: The crude residue from the oxidation was dissolved in DCM (3.2 mL) and cooled to 0° C. To this solution was added DBU (50 μL, 0.33 mmol) dropwise, and the mixture was allowed to warm to r.t. After stirring for 15 min, the mixture was diluted with DCM (10 mL), washed with 1N HCl (10 mL), water (10 mL), and finally brine (10 mL). The organic layer was dried over MgSO$_4$, filtered, and concentrated under reduced pressure. The resulting crude material was purified using a Biotage Isolera Prime with two columns (SiO$_2$, 10-80% EtOAc in hexanes, then 0-8% MeOH in DCM). A white residue (8.9 mg, 8.4% over three steps) was obtained. $^1$H NMR (400 MHz, Chloroform-d) δ 7.77 (dt, J=8.3, 1.9 Hz, 2H), 7.61-7.48 (m, 1H), 7.37-7.28 (m, 3H), 7.28-7.20 (m, 2H), 7.17 (dt, J=9.1, 4.8 Hz, 1H), 7.10 (d, J=7.5 Hz, 2H), 7.02 (dt, J=14.7, 2.0 Hz, 1H), 6.15 (d, J=6.6 Hz, 1H), 4.50 (q, J=7.0 Hz, 1H), 3.27 (ddd, J=40.4, 13.6, 6.7 Hz, 2H), 2.64 (s, 2H), 2.43 (s, 3H), 2.15 (dd, J=14.2, 7.1 Hz, 1H), 2.00 (dq, J=14.7, 7.4 Hz, 1H), 1.57 (dq, J=13.5, 6.7 Hz, 1H), 1.43-1.32 (m, 2H), 0.88 (dd, J=6.5, 1.8 Hz, 6H). $^{13}$C NMR (126 MHz, CDCl$_3$) δ 171.16, 162.51, 145.54, 141.05, 140.65, 136.03, 133.67, 133.18, 130.37, 130.06, 128.83, 128.69, 128.57, 128.55, 126.52, 77.54, 77.28, 77.03, 53.61, 38.40, 38.34, 34.43, 32.02, 26.03, 22.68, 22.61, 21.96. HRMS (ESI) m/z: calculated. R$_f$ 0.32 (3% MeOH in DCM).

REFERENCES (1) Jemal, A., Siegel, R., Ward, E., Murray, T., Xu, J., and Thun, M. J. (2007) Cancer Statistics, 2007. *CA. Cancer J. Clin.* 57, 43-66.

(2) Obeng, E. A., Carlson, L. M., Gutman, D. M., Harrington, W. J., Lee, K. P., and Boise, L. H. (2006) Proteasome inhibitors induce a terminal unfolded protein response in multiple myeloma cells. *Blood* 107, 4907-4916.

(3) Kumar, S. K., Rajkumar, S. V., Dispenzieri, A., Lacy, M. Q., Hayman, S. R., Buadi, F. K., Zeldenrust, S. R., Dingli, D., Russell, S. J., Lust, J. A., Greipp, P. R., Kyle, R. A., and Gertz, M. A. (2008) Improved survival in multiple myeloma and the impact of novel therapies. *Blood* 111, 2516 LP-2520.

(4) Moreau, P., Richardson, P. G., Cavo, M., Orlowski, R. Z., San Miguel, J. F., Palumbo, A., and Harousseau, J.-L. (2012) Proteasome inhibitors in multiple myeloma: 10 years later. *Blood* 120, 947 LP-959.

(5) Ciechanover, A. (1994) The ubiquitin-proteasome proteolytic pathway. *Cell* 79, 13-21.

(6) Adams, J. (2003) The proteasome: structure, function, and role in the cell. *Cancer Treat. Rev.* 29,3-9.

(7) Ciechanover, A. (1998) The ubiquitin-proteasome pathway: on protein death and cell life. *EMBO J.* 17, 7151 LP-7160.

(8) Dou, Q. P., and Li, B. (2016) Proteasome inhibitors as potential novel anticancer agents. *Drug Resist. Updat.* 2,215-223.

(9) Adams, J. (2004) The proteasome: a suitable antineoplastic target. *Nat Rev Cancer* 4, 349-360.

(10) Dou, Q. P., and Zonder, J. A. (2014) Overview of Proteasome Inhibitor-Based Anti-cancer Therapies: Perspective on Bortezomib and Second Generation Proteasome Inhibitors versus Future Generation Inhibitors of Ubiquitin-Proteasome System. *Curr. Cancer Drug Targets* 14, 517-536.

(11) Hideshima, T., Richardson, P., Chauhan, D., Palombella, V. J., Elliott, P. J., Adams, J., and Anderson, K. C. (2001) The proteasome inhibitor PS-341 inhibits growth, induces apoptosis, and overcomes drug resistance in human multiple myeloma cells. *Cancer Res* 61.

(12) Hideshima, T., Chauhan, D., Richardson, P., Mitsiades, C., Mitsiades, N., Hayashi, T., Munshi, N., Dang, L., Castro, A., Palombella, V., Adams, J., and Anderson, K. C. (2002) NF-kappa B as a therapeutic target in multiple myeloma. *J Biol Chem* 277.

(13) Hideshima, T., Chauhan, D., Hayashi, T., Akiyama, M., Mitsiades, N., Mitsiades, C., Podar, K., Munshi, N. C., Richardson, P. G., and Anderson, K. C. (2003) Proteasome inhibitor PS-341 abrogates IL-6 triggered signaling cascades via caspase-dependent downregulation of gp130 in multiple myeloma. *Oncogene* 22.

(14) Boccadoro, M., Morgan, G., and Cavenagh, J. (2005) Preclinical evaluation of the proteasome inhibitor bortezomib in cancer therapy. *Cancer Cell Int.* 5, 18.

(15) Reddy, N., and Czuczman, M. S. (2010) Enhancing activity and overcoming chemoresistance in hematologic malignancies with bortezomib: preclinical mechanistic studies. *Ann. Oncol.* 21, 1756-1764.

(16) Qin, J.-Z., Ziffra, J., Stennett, L., Bodner, B., Bonish, B. K., Chaturvedi, V., Bennett, F., Pollock, P. M., Trent, J. M., Hendrix, M. J. C., Rizzo, P., Miele, L., and Nickoloff, B. J. (2005) Proteasome Inhibitors Trigger NOXA-Mediated Apoptosis in Melanoma and Myeloma Cells. *Cancer Res.* 65, 6282 LP-6293.

(17) Oda, E., Ohki, R., Murasawa, H., Nemoto, J., Shibue, T., Yamashita, T., Tokino, T., Taniguchi, T., and Tanaka, † Nobuyuki. (2000) Noxa, a BH3-Only Member of the Bcl-2 Family and Candidate Mediator of p53-Induced Apoptosis. *Science (80-.).* 288, 1053 LP-1058.

(18) Lü, S., and Wang, J. (2013) The resistance mechanisms of proteasome inhibitor bortezomib. *Biomark. Res.* 1, 13.

(19) Jain, S., Diefenbach, C., Zain, J., and O'Connor, O. A. (2011) Emerging role of carfilzomib in treatment of relapsed and refractory lymphoid neoplasms and multiple myeloma. *Core Evid.* 6, 43-57.

(20) Arastu-Kapur, S., Anderl, J. L., Kraus, M., Parlati, F., Shenk, K. D., Lee, S. J., Muchamuel, T., Bennett, M. K., Driessen, C., Ball, A. J., and Kirk, C. J. (2011) Nonproteasomal Targets of the Proteasome Inhibitors Bortezomib and Carfilzomib: a Link to Clinical Adverse Events. *Clin. Cancer Res.* 17, 2734 LP-2743.

(21) Kuhn, D. J., Chen, Q., Voorhees, P. M., Strader, J. S., Shenk, K. D., Sun, C. M., Demo, S. D., Bennett, M. K., van Leeuwen, F. W. B., Chanan-Khan, A. A., and Orlowski, R. Z. (2007) Potent activity of carfilzomib, a novel, irreversible inhibitor of the ubiquitin-proteasome pathway, against preclinical models of multiple myeloma. *Blood* 110, 3281 LP-3290.

(22) Kim, H. M., Han, J. W., and Chan, J. Y. (2016) Nuclear Factor Erythroid-2 Like 1 (NFE2L1): Structure, function and regulation. *Gene* 584, 17-25.

(23) Zhang, Y., and Xiang, Y. (2016) Molecular and cellular basis for the unique functioning of Nrf1, an indispensable transcription factor for maintaining cell homoeostasis and organ integrity. *Biochem. J.* 473, 961 LP-1000.

(24) Sha, Z., and Goldberg, A. L. (2014) Proteasome-Mediated Processing of Nrf1 Is Essential for Coordinate Induction of All Proteasome Subunits and p97. *Curr. Biol.* 24, 1573-1583.

(25) Zhang, Y., Lucocq, J. M., Yamamoto, M., and Hayes, J. D. (2007) The NHB1 (N-terminal homology box 1) sequence in transcription factor Nrf1 is required to anchor it to the endoplasmic reticulum and also to enable its asparagine-glycosylation. *Biochem. J.* 408, 161-172.

(26) Lehrbach, N. J., and Ruvkun, G. (2016) Proteasome dysfunction triggers activation of SKN-1A/Nrf1 by the aspartic protease DDI-1. *bioRxiv*.

(27) Koizumi, S., Irie, T., Hirayama, S., Sakurai, Y., Yashiroda, H., Naguro, I., Ichijo, H., Hamazaki, J., and Murata, S. (2016) The aspartyl protease DDI2 activates Nrf1 to compensate for proteasome dysfunction. *Elife* (Dikic, I., Ed.) 5, e18357.

(28) Radhakrishnan, S. K., den Besten, W., and Deshaies, R. J. (2014) p97-dependent retrotranslocation and proteolytic processing govern formation of active Nrf1 upon proteasome inhibition. *Elife* (Brown, M. S., Ed.) 3, e01856.

(29) Zhang, Y., Qiu, L., Li, S., Xiang, Y., Chen, J., and Ren, Y. (2014) The C-Terminal Domain of Nrf1 Negatively Regulates the Full-Length CNC-bZIP Factor and Its Shorter Isoform LCR-F1/Nrf1β; Both Are Also Inhibited by the Small Dominant-Negative Nrf1γ/δ Isoforms that Down-Regulate ARE-Battery Gene Expression. *PLoS One* 9, e109159.

(30) Zhang, Y., Ren, Y., Li, S., and Hayes, J. D. (2014) Transcription Factor Nrf1 Is Topologically Repartitioned across Membranes to Enable Target Gene Transactivation through Its Acidic Glucose-Responsive Domains. *PLoS One* 9, e93458.

(31) Radhakrishnan, S. K., Lee, C. S., Young, P., Beskow, A., Chan, J. Y., and Deshaies, R. J. (2010) Transcription factor Nrf1 mediates the proteasome recovery pathway after proteasome inhibition in mammalian cells. *Mol. Cell* 38, 17-28.

(32) Hirsch, C., Blom, D., and Ploegh, H. L. (2003) A role for N-glycanase in the cytosolic turnover of glycoproteins. *EMBO J.* 22,1036 LP-1046.

(33) Suzuki, T., Seko, A., Kitajima, K., Inoue, Y., and Inoue, S. (1993) Identification of Peptide:N-Glycanase Activity in Mammalian-Derived Cultured Cells. *Biochem. Biophys. Res. Commun.* 194, 1124-1130.

(34) Suzuki, T., Park, H., Hollingsworth, N. M., Sternglanz, R., and Lennarz, W. J. (2000) PNG1, a Yeast Gene Encoding a Highly Conserved Peptide:<em>N</em>-Glycanase. *J. Cell Biol.* 149, 1039 LP-1052.

Radhakrishnan, S. K., Lee, C. S., Young, P., Beskow, A., Chan, J. Y., and Deshaies, R. J. (2010) Transcription factor Nrf1 mediates the proteasome recovery pathway after proteasome inhibition in mammalian cells. *Mol. Cell* 38, 17-28.

Radhakrishnan, S. K., den Besten, W., and Deshaies, R. J. (2014) p97-dependent retrotranslocation and proteolytic processing govern formation of active Nrf1 upon proteasome inhibition. *Elife* (Brown, M. S., Ed.) 3, e01856.

Gilbert, L. A.; Horlbeck, M. A.; Adamson, B.; Villalta, J. E.; Chen, Y.; Whitehead, E. H.; Guimaraes, C.; Panning, B.; Ploegh, H. L.; Bassik, M. C.; Qi, L. S.; Kampmann, M.; Weissman, J. S. *Cell* 2014, 159 (3), 647-661.

Horlbeck, M. A.; Gilbert, L. A.; Villalta, J. E.; Adamson, B.; Pak, R. A.; Chen, Y.; Fields, A. P.; Park, C. Y.; Corn, J. E.; Kampmann, M.; Weissman, J. S. *eLife* 2016, 5, e19760.

Gilbert, L. A.; Larson, M. H.; Morsut, L.; Liu, Z.; Brar, G. A.; Torres, S. E.; Stern-Ginossar, N.; Brandman, O.; Whitehead, E. H.; Doudna, J. A.; Lim, W. A.; Weissman, J. S.; Qi, L. S. *Cell* 2013, 154 (2), 442-451.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of treating cancer, the method comprising: contacting cancer cells with an Ngly1 inhibitor that does not inhibit caspase activity, wherein said Ngly1 inhibitor is in a dose effective to reduce expression of a cancer cell proteasome; and concomitant administration of a direct proteasome inhibitor in a dose effective to inhibit proteasome activity in the cancer cells, wherein the number of viable cancer cells is reduced.

2. The method of claim 1, wherein the direct proteasome inhibitor is one or more of bortezomib, carfilzomib, ixazomib, delanzomib, oprozomib, marizomib, IPSI-001, ONX-0914, and PR-924.

3. The method of claim 1 wherein a combination of Ngly1 inhibitor and direct proteasome inhibitor provides for a synergistic effect in reducing the number of viable cancer cells relative to the administration of either agent as a single agent.

4. The method of claim 1, wherein the dose of direct proteasome inhibitor effective to inhibit proteasome activity in the cancer cells is lower than the effective dose to inhibit proteasome activity in the absence of the Ngly1 inhibitor.

5. The method of claim 1, wherein the period of time over which the direct proteasome inhibitor is effective is longer than the period of time it is effective in the absence of the Ngly1 inhibitor.

6. The method of claim 1, wherein the cancer is a hematologic cancer.

7. The method of claim 6, wherein the hematologic cancer is multiple myeloma.

8. The method of claim 1, wherein the Ngly1 inhibitor inhibits Ngly1 mechanistically by inhibiting nucleophilic attack of a cysteine residue at an amide linkage between an asparagine side chain of a target protein and N-linked oligosaccharide.

9. The method of claim 1, wherein the Ngly1 inhibitor has a structure of Formula I:

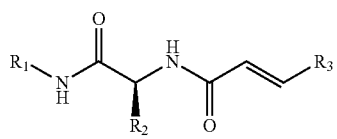

where R₁ is H, alkyl, substituted alkyl, aryl, alkaryl, substituted aryl, or substituted alkaryl;

R₂ is H, alkyl, substituted alkyl, aryl, alkaryl, substituted aryl, or substituted alkaryl; and R₃ is alkyl, substituted alkyl, aryl, alkaryl, substituted aryl, substituted alkaryl, an electron withdrawing substituent, or an electron donating group.

10. The method of claim 1, wherein the Ngly1 inhibitor has a structure of formula II:

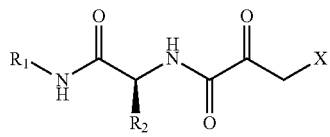

where R₁ is H, alkyl, substituted alkyl, aryl, alkaryl, substituted aryl, or substituted alkaryl;

R₂ is H, alkyl, substituted alkyl, aryl, alkaryl, substituted aryl, or substituted alkaryl; and where X is a chloro, bromo, fluoro or iodo substituent.

11. The method of claim 9, wherein the Ngly1 inhibitor has a structure of Formula III:

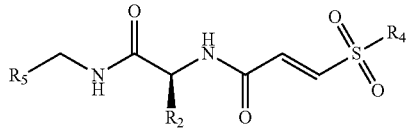

R₄ is an alkyl group;

R₅ is polar or alkynyl, alkenyl, morpholino, amino, amido, or sulfhydryl.

12. The method of claim 1, wherein the Ngly1 inhibitor has a structure of Formula IV:

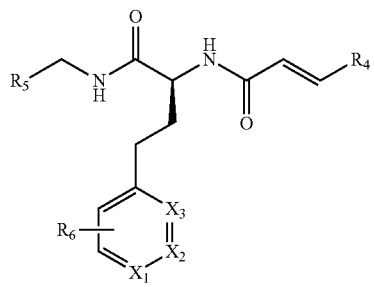

wherein R₄ is an alkyl group;

R₅ is polar or an alkynyl, alkenyl, morpholino, amino, amido, or sulfhydryl;

R₆ is an optional substituent on the aryl ring, which substitutent is alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl, —SO₂-heteroaryl, or fused heterocycle; and any of X₁, X₂ and X₃ are optionally a heteroatom in the aryl ring selected from nitrogen, oxygen, sulfur, phosphorus or silicon, and are carbon if not a heteroatom.

13. The method of claim 1 wherein the Ngly1 inhibitor is:

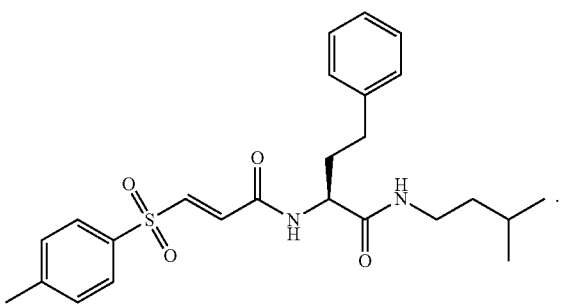 [SMILES: Cc1ccc(S(=O)(=O)/C=C/C(=O)N[C@@H](CCc2ccccc2)C(=O)NCCC(C)C)cc1]

14. The method of claim 1, wherein the Ngly1 inhibitor is an epoxyketone of Formula V

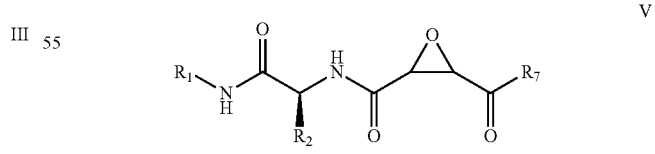

where R₁ is H, alkyl, substituted alkyl, aryl, alkaryl, substituted aryl, or substituted alkaryl;

R₂ is H, alkyl, substituted alkyl, aryl, alkaryl, substituted aryl, or substituted alkaryl; and where R₇ is an amine, substituted amine, amide, substituted amide, alkyl substituted alkyl, aryl, alkaryl, substituted aryl, or substituted alkaryl.

15. A composition, comprising an Ngly1 inhibitor in a unit dose effective to reduce proteasome expression in a targeted cell; and a direct proteasome inhibitor in a unit dose effective to inhibit proteasome activity.

* * * * *